(12) United States Patent
Proudhon et al.

(10) Patent No.: US 12,371,741 B2
(45) Date of Patent: Jul. 29, 2025

(54) METHOD FOR DETECTING A MUTATION IN A MICROSATELLITE SEQUENCE

(71) Applicants: Institut Curie, Paris (FR); Institut National de la Sante et de la Recherche Medicale, Paris (FR); Universite de Versailles Saint-Quentin-en-Yvelines, Versailles (FR)

(72) Inventors: Charlotte Proudhon, Pantin (FR); Amélie Kasperek, Paris (FR); Amanda Bortolini Silveira, Paris (FR); François-Clément Bidard, Paris (FR); Marc-Henri Stern, Paris (FR)

(73) Assignees: Institut Curie, Paris (FR); Institut National de la Sante et de la Recherche Medicale, Paris (FR); Universite de Versailles Saint-Quentin-en-Yvelines, Versailles (FR)

( * ) Notice: Subject to any disclaimer, the term of this patent is extended or adjusted under 35 U.S.C. 154(b) by 0 days.

(21) Appl. No.: 18/434,179

(22) Filed: Feb. 6, 2024

(65) Prior Publication Data

US 2024/0229122 A1     Jul. 11, 2024

Related U.S. Application Data

(63) Continuation of application No. 17/933,946, filed on Sep. 21, 2022, now abandoned, which is a continuation of application No. 16/629,150, filed as application No. PCT/EP2018/068760 on Jul. 11, 2018, now abandoned.

(30) Foreign Application Priority Data

Jul. 12, 2017 (EP) .................................... 17305920

(51) Int. Cl.
C12Q 1/6858 (2018.01)
C12Q 1/6886 (2018.01)
G01N 21/64 (2006.01)

(52) U.S. Cl.
CPC ......... *C12Q 1/6858* (2013.01); *C12Q 1/6886* (2013.01); *G01N 21/6428* (2013.01); *C12Q 2600/156* (2013.01); *G01N 2021/6439* (2013.01)

(58) Field of Classification Search
CPC .................... C12Q 2563/159; C12Q 2600/156
See application file for complete search history.

(56) References Cited

U.S. PATENT DOCUMENTS

| | | | |
|---|---|---|---|
| 2003/0113723 A1 | 6/2003 | Bapat et al. | |
| 2006/0019277 A1 | 1/2006 | Traverso et al. | |
| 2013/0183666 A1 | 7/2013 | Feiglin et al. | |
| 2014/0287937 A1 | 9/2014 | So et al. | |

FOREIGN PATENT DOCUMENTS

| | | |
|---|---|---|
| CN | 106834479 A | 6/2017 |
| JP | 2005-516603 A | 6/2005 |
| JP | 2015-516144 A | 6/2015 |
| WO | 2017/050934 A1 | 3/2017 |

OTHER PUBLICATIONS

International Search Report issued in corresponding International Patent Application No. PCT/EP2018/068760 dated Aug. 2, 2018.
Written Opinion issued in corresponding International Patent Application No. PCT/EP2018/068760 dated Aug. 2, 2018.
Dietmaier et al., "Detection of Microsatellite Instability by Real Time PCR and Hybridization Probe Melting Point Analysis," Laboratory Investigation, 81: 1453-1456 (2001).
Bidshahri et al., "Quantitative Detection and Resolution of BRAF V600 Status in Colorectal Cancer Using Droplet Digital PCR and a Novel Wild-Type Negative Assay," Journal of Molecular Diagnostics, 18: 190-204 (2016).
Hause et al., "Classification and characterization of microsatellite instability across 18 cancer types," Nature Medicine, 22: 1342-1350 (2016).
Mokarram et al., "Microsatellite instability typing in serum and tissue of patients with colorectal cancer: comparing real time PCR with hybridization probe and high-performance liquid chromatography," Molecular Biology Reports, 41: 2835-2844 (2014).
Yan et al., "Prediction of biological behavior and prognosis of colorectal cancer patients by tumor MSI/MMR in the Chinese population," Onco Targets and Therapy, 9: 7415-7424 (2016).
Cabel et al., "Circulating tumor DNA changes for early monitoring of anti-PD1 immunotherapy: a proof-of-concept study," Annals of Oncology, 28: 8 (2017).

(Continued)

*Primary Examiner* — Young J Kim
(74) *Attorney, Agent, or Firm* — Morgan, Lewis & Bockius LLP

(57) ABSTRACT

The present disclosure relates to a method for detecting a mutation in a microsatellite sequence locus of a target fragment from a DNA sample, comprising a step of subjecting said DNA sample to a digital polymerase chain reaction (PCR) in the presence of a PCR solution comprising:

Figure 1:
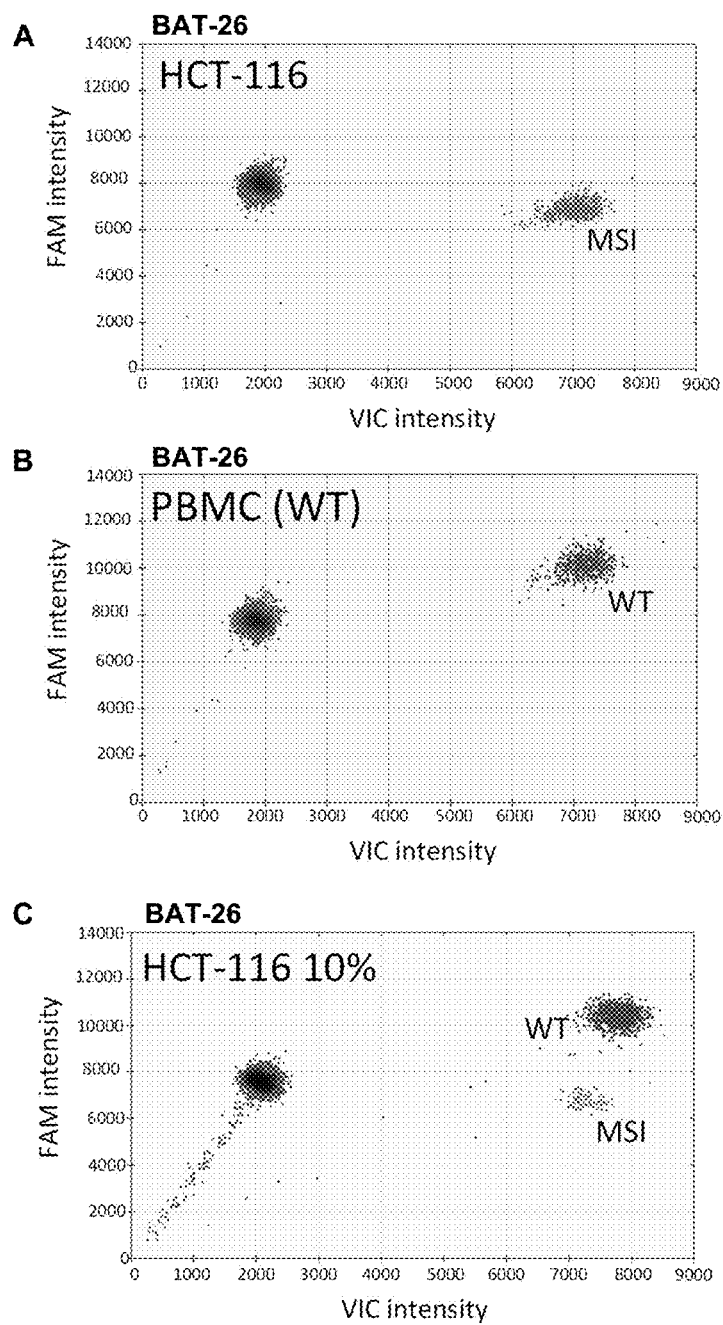
Figure 1:
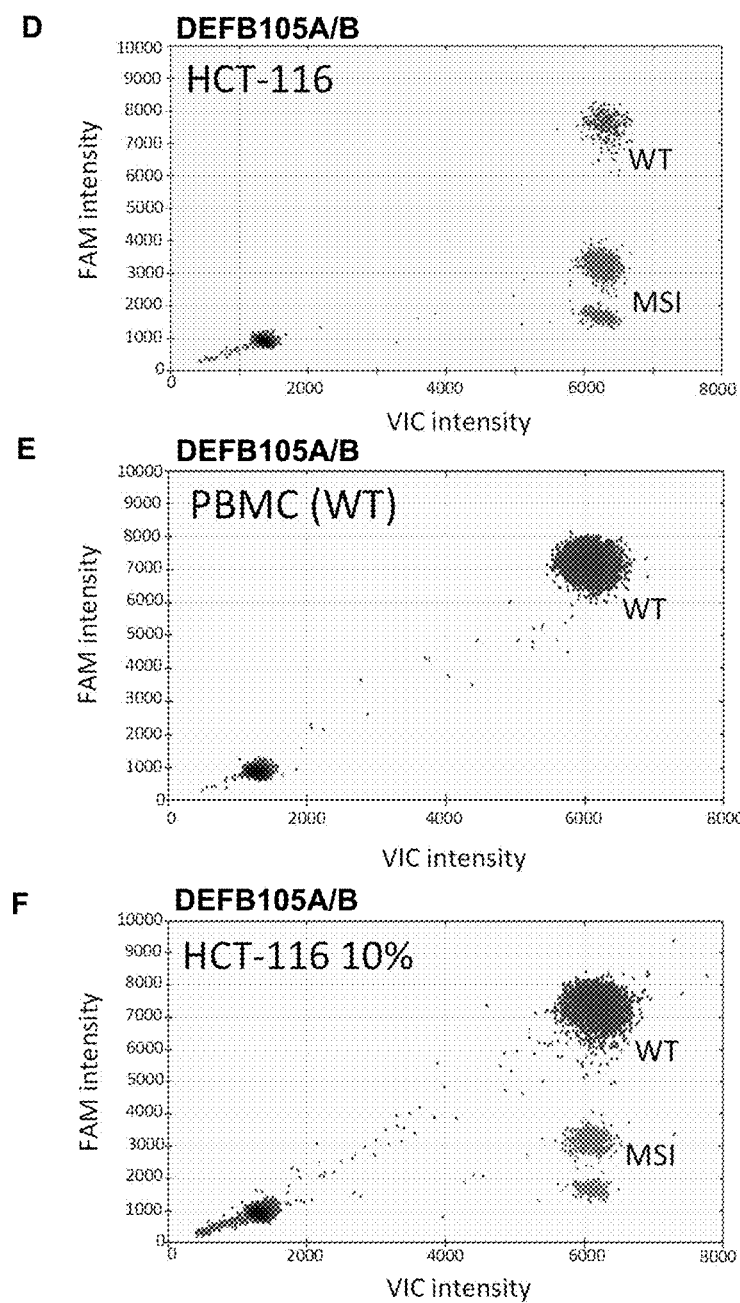
Figure 1:
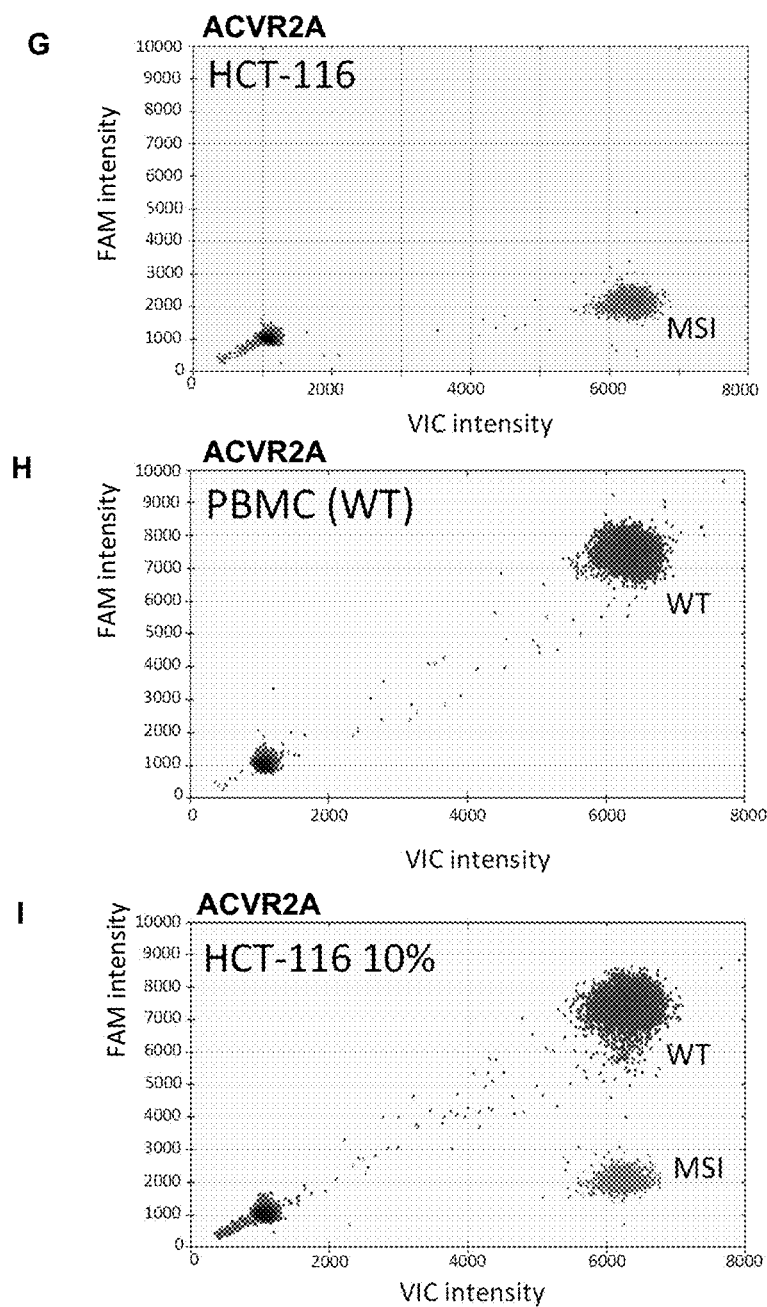

a pair of primers suitable for amplifying said target fragment of the DNA sample including said microsatellite sequence;

a first MS oligonucleotide (MS) hydrolysis probe, labeled with a first fluorophore, wherein said first MS oligonucleotide probe is complementary to a wild-type sequence including the microsatellite sequence;

a second oligonucleotide reference (REF) hydrolysis probe, labeled with a second fluorophore, wherein said second oligonucleotide REF probe is complementary to a wild-type sequence of said target DNA fragment which does not include said microsatellite sequence.

9 Claims, 6 Drawing Sheets

Specification includes a Sequence Listing.

(56) References Cited

OTHER PUBLICATIONS

Xiao et al., "The Microsatellite Instable Subset of Colorectal Cancer is Particularly Good Candidate for Checkpoint Blockade Immunotherapy," Cancer Discovery, 16-18 (2015).
Notice of Intent to Grant issued in corresponding European Patent Application No. 18736935.0 dated Nov. 29, 2023.
Decision to Grant issued in corresponding European Patent Application No. 18736935.0 dated Mar. 21, 2024.
Office Action issued in corresponding European Patent Application No. 18736935.0 dated Apr. 26, 2023.

SEQUENCE LISTING

```
Sequence total quantity: 20
SEQ ID NO: 1           moltype = DNA  length = 31
FEATURE                Location/Qualifiers
misc_feature           1..31
                       note = primer
source                 1..31
                       mol_type = other DNA
                       organism = synthetic construct
SEQUENCE: 1
gacttcagcc agtatatgaa attggatatt g                                31

SEQ ID NO: 2           moltype = DNA  length = 36
FEATURE                Location/Qualifiers
misc_feature           1..36
                       note = primer
source                 1..36
```

```
                          mol_type = other DNA
                          organism = synthetic construct
SEQUENCE: 2
gtatatgtca atgaaaacat ttttttaacca ttcaac                             36

SEQ ID NO: 3              moltype = DNA   length = 23
FEATURE                   Location/Qualifiers
misc_feature              1..23
                          note = Probe
source                    1..23
                          mol_type = other DNA
                          organism = synthetic construct
SEQUENCE: 3
agcagtcaga gcccttaacc ttt                                            23

SEQ ID NO: 4              moltype = DNA   length = 33
FEATURE                   Location/Qualifiers
misc_feature              1..33
                          note = Probe
source                    1..33
                          mol_type = other DNA
                          organism = synthetic construct
SEQUENCE: 4
aggtaaaaaa aaaaaaaaaa aaaaaaaaaa agg                                 33

SEQ ID NO: 5              moltype = DNA   length = 22
FEATURE                   Location/Qualifiers
misc_feature              1..22
                          note = Primer
source                    1..22
                          mol_type = other DNA
                          organism = synthetic construct
SEQUENCE: 5
gaggaggaaa ttggccagca tc                                             22

SEQ ID NO: 6              moltype = DNA   length = 25
FEATURE                   Location/Qualifiers
misc_feature              1..25
                          note = Primer
source                    1..25
                          mol_type = other DNA
                          organism = synthetic construct
SEQUENCE: 6
agctaactgg ataacttaca gcatg                                          25

SEQ ID NO: 7              moltype = DNA   length = 22
FEATURE                   Location/Qualifiers
misc_feature              1..22
                          note = Probe
source                    1..22
                          mol_type = other DNA
                          organism = synthetic construct
SEQUENCE: 7
acttcctgca tgtcttcaag ag                                             22

SEQ ID NO: 8              moltype = DNA   length = 16
FEATURE                   Location/Qualifiers
misc_feature              1..16
                          note = Probe
source                    1..16
                          mol_type = other DNA
                          organism = synthetic construct
SEQUENCE: 8
cctctttttt ttatgc                                                    16

SEQ ID NO: 9              moltype = DNA   length = 25
FEATURE                   Location/Qualifiers
misc_feature              1..25
                          note = Primer
source                    1..25
                          mol_type = other DNA
                          organism = synthetic construct
SEQUENCE: 9
ttgaaaaatc tgggctgatt cttga                                          25

SEQ ID NO: 10             moltype = DNA   length = 22
FEATURE                   Location/Qualifiers
misc_feature              1..22
                          note = Primer
```

```
source                  1..22
                        mol_type = other DNA
                        organism = synthetic construct
SEQUENCE: 10
tgagggagct ttccaggaaa tg                                               22

SEQ ID NO: 11           moltype = DNA   length = 24
FEATURE                 Location/Qualifiers
misc_feature            1..24
                        note = Probe
source                  1..24
                        mol_type = other DNA
                        organism = synthetic construct
SEQUENCE: 11
ctttgacatg ttccccattt ctag                                             24

SEQ ID NO: 12           moltype = DNA   length = 16
FEATURE                 Location/Qualifiers
misc_feature            1..16
                        note = Probe
source                  1..16
                        mol_type = other DNA
                        organism = synthetic construct
SEQUENCE: 12
tccctttttt tttggt                                                      16

SEQ ID NO: 13           moltype = DNA   length = 27
FEATURE                 Location/Qualifiers
misc_feature            1..27
                        note = Primer
source                  1..27
                        mol_type = other DNA
                        organism = synthetic construct
SEQUENCE: 13
tgaagacctc acagtaaaaa taggtga                                          27

SEQ ID NO: 14           moltype = DNA   length = 21
FEATURE                 Location/Qualifiers
misc_feature            1..21
                        note = Primer
source                  1..21
                        mol_type = other DNA
                        organism = synthetic construct
SEQUENCE: 14
actgatggga cccactccat c                                                21

SEQ ID NO: 15           moltype = DNA   length = 15
FEATURE                 Location/Qualifiers
misc_feature            1..15
                        note = Probe
source                  1..15
                        mol_type = other DNA
                        organism = synthetic construct
SEQUENCE: 15
tagctacagt gaaat                                                       15

SEQ ID NO: 16           moltype = DNA   length = 16
FEATURE                 Location/Qualifiers
misc_feature            1..16
                        note = Probe
source                  1..16
                        mol_type = other DNA
                        organism = synthetic construct
SEQUENCE: 16
ctagctacag agaaat                                                      16

SEQ ID NO: 17           moltype = DNA   length = 24
FEATURE                 Location/Qualifiers
misc_feature            1..24
                        note = Primer
source                  1..24
                        mol_type = other DNA
                        organism = synthetic construct
SEQUENCE: 17
cagcatgttt ctgccaataa tctc                                             24

SEQ ID NO: 18           moltype = DNA   length = 18
FEATURE                 Location/Qualifiers
misc_feature            1..18
```

```
                        note = Probe
source                  1..18
                        mol_type = other DNA
                        organism = synthetic construct
SEQUENCE: 18
aggcctcttt tttttatg                                                      18

SEQ ID NO: 19           moltype = DNA  length = 20
FEATURE                 Location/Qualifiers
misc_feature            1..20
                        note = Primer
source                  1..20
                        mol_type = other DNA
                        organism = synthetic construct
SEQUENCE: 19
gccaagaaag agctgctgag                                                    20

SEQ ID NO: 20           moltype = DNA  length = 21
FEATURE                 Location/Qualifiers
misc_feature            1..21
                        note = Probe
source                  1..21
                        mol_type = other DNA
                        organism = synthetic construct
SEQUENCE: 20
aactgtccct ttttttttgg t                                                  21
```

METHOD FOR DETECTING A MUTATION IN A MICROSATELLITE SEQUENCE

INTRODUCTION

Microsatellites (MS) are tandem repeats of short DNA sequences that are abundant throughout the human genome. Owing to their high mutation rates, microsatellite sequences have been widely used as polymorphic markers in population genetics and forensics. Microsatellite instability (MSI) is a hypermutator phenotype that occurs in tumors with impaired DNA mismatch repair (MMR) and is characterized by widespread length polymorphisms of microsatellite repeats due to DNA polymerase slippage as well as by elevated frequency of single-nucleotide variants (SNVs). MSI is caused by inactivation of MMR genes (for example, MLH1, MSH2, MSH3, MSH6 and PMS2) through somatic mutations, with increased risk of cancer for those with inherited germline mutations (that is, Lynch syndrome). MSI also occurs by epigenetic inactivation of MMR genes (for example hypermethylation of the MLH1 and MSH2 promoters associated with the somatic BRAF V600E mutation or deletion in the 3' end of Ep-CAM), or downregulation of MMR genes by microRNAs. MSI events within coding regions can alter the reading frame, leading to truncated functionally-impaired proteins (see also Cortes-Ciriano et al., Nat Commun. 2017 Jun. 6; 8:15180 and Copija et al., Int J Mol Sci. 2017 Jan. 6; 18(1). pii: E107).

The MSI phenotype has been largely used as a molecular diagnostic tool for gastrointestinal, endometrial and colorectal tumors, where it has important implications for disease prognosis and rational planning of treatment (Boland and Goel, Gastroenterology 2010 June; 138(6):2073-2087.e3, Copija et al., Int J Mol Sci. 2017 Jan. 6; 18(1). pii: E107). MSI positive tumors are known to display unique histopathological and clinical features including specific location, poor differentiation, high lymphocytic infiltration and better prognosis associated with low frequency of distant metastasis (Boland and Goel, Gastroenterology 2010; 138 (6):2073-2087.e3).

Recent analyses have also identified MSI across several additional cancer types, such as urinary tract, ovarian, prostate, lung, head and neck, liver and glioblastomas, suggesting a potential broader application of MSI screening in clinical practice (Hause et al., Nat Med. 2016 November; 22(11):1342-1350, Cortes-Ciriano et al., Nat Commun. 2017 Jun. 6; 8:15180).

Indeed, MSI has recently emerged as the first pan-tumor biomarker likely to predict clinical benefit from immune-checkpoint blockade therapy (Le et al., N Engl J Med. 2015 Jun. 25; 372(26):2509-20; Le et al., Science 2017 Jun. 8. pii: eaan6733). Remarkably, via an Accelerated Approval process, the FDA has recently granted the use of anti-PD-1 blockade therapy for the treatment of adult and pediatric patients with unresectable or metastatic MSI positive or MMR-deficient solid tumors.

Molecular diagnosis of MSI is currently done by examining PCR products of a few informative microsatellite loci of DNA extracted from tumor samples (Bacher et al., Disease Markers 2004, 237-250). Disadvantages of this method include the requirement of capillary electrophoresis for detection of shifts in allele size and the limited sensitivity of the technique, which requires a minimum tumor cellularity of 20% to achieve reliable and robust results (Shi and Washington, Am J Clin Pathol 2012 137:847-859). Recently, next generation sequencing methods (NGS) have been used for higher sensitivity and better precision in MSI detection (Salipante et al., Clin Chem 2014 Jun. 30 60 (9), 1192-1199; Hause et al., Nat Med. 2016 November; 22(11):1342-1350, Cortes-Ciriano et al., Nat Commun. 2017 Jun. 6; 8:15180). Although clearly an improvement over the method currently used in clinics, the sensitivity of 1% obtained by NGS still remains above the sensitivity of PCR-based assays.

Thus the development of a sensitive MSI diagnostic method usable on circulating tumor DNA obtained from liquid biopsies remains of high clinical and therapeutic importance.

SUMMARY OF THE INVENTION

The authors have designed a digital PCR diagnostic method for detecting microsatellite instability, which can be performed on a DNA sample containing a very low concentration of target DNA.

The authors have indeed demonstrated that the achieved limit of detection (i.e., the lowest concentration likely to be reliably distinguished from the limit of blank and at which the detection is feasible), is 250 fold lower than the minimum cellularity threshold (i.e. at least 20% cellularity) required to determine the MSI status by the pentaplex assay currently applied in clinical practice (see Bacher et al 2004, Disease Markers 20:237-250, see also Shi and Washington, Am J Clin Pathol 2012 137:847-859). According to the results as shown herein the present new MSI detection assay is both highly specific and sensitive, as sensitivity could reach values, at least in theory, approaching 0.1%. This innovative approach also offers several other advantages including the simplicity of blood tests and reduced time of analysis. Taken together, the MSI diagnostic method of the invention promises better diagnostic accuracy and the unprecedented use of a MSI biomarker in liquid biopsies for diagnosis and monitoring of disease treatment and disease progression.

A similar technique has been previously used for the detection of BRAF status in colorectal cancer (see Bidshahri et al., The Journal of Molecular Diagnostic 2016, 18(2): 190-204). However, the use of such a technique has never been envisioned for the detection of a mutated microsatellite sequence. Indeed, due to the size and more particularly to the extreme repetitive nature of the microsatellite sequence, it would be expected that the probe covering the microsatellite (MS probe, see below) would slip over the repeat sequence such that efficient or reliable hybridization of the probe could not be obtained.

Dietmaier et al. (Laboratory Investigation, 2001) describe a technique for the detection of a microsatellite sequence by RT-PCR and by analyzing the melting point, using hybridization probes of specific sequences of the targeted markers. The Light Cycler HybProbes hybridization probes used in this document are not capable of discriminating WT and mutant microsatellite sequences. Therefore additional melting point analyses are required after real time PCR amplification for identification of mutated microsatellites. Besides, the probes of Dietmaier et al. are not regarded as hydrolysis probes and are not relevant in the context of a digital PCR reaction.

The method of the invention is based on a single reaction with two hydrolysis probes located within the same amplicon. The first one covers the full WT microsatellite sequence (MS probe). The second one is a reference probe (REF) located in a non-variable region, which does not include the microsatellite sequence (MS) locus and is used to quantify droplets with amplifiable DNA. Therefore, wild-type (WT) sequences will display a double positive fluorescence signal coming from the hybridization of both the REF and MS probes, while droplets containing mutated microsatellite alleles will present a shifted signal that results from the hybridization of the REF probe only.

The present invention therefore relates to a method for detecting a mutation in a microsatellite sequence locus of a target fragment from a DNA sample, comprising a step of subjecting said DNA sample to a digital polymerase chain reaction (dPCR) in the presence of a PCR solution comprising:

a pair of primers suitable for amplifying said target fragment of the DNA sample including said microsatellite sequence;

a first oligonucleotide microsatellite (MS) hydrolysis probe, labeled with a first fluorophore, wherein said first MS oligonucleotide probe is complementary to a wild-type sequence including the microsatellite sequence;

a second oligonucleotide reference (REF) hydrolysis probe, labeled with a second fluorophore, wherein said second oligonucleotide REF probe is complementary to a wild-type sequence of said target DNA fragment, which does not include said microsatellite sequence.

Preferably, the digital PCR (dPCR) is digital droplet PCR (ddPCR).

The target fragment of the DNA sample can be constitutional genomic DNA or genomic tumor DNA or circulating DNA.

The microsatellite sequence locus can be selected from the group comprising BAT-25, BAT-26, BAT-34c4, BAT-40, NR21, NR24, MONO-27, D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1. In addition, microsatellite sequences located in regions of the genome frequently amplified in cancer (e.g. chr8q region of the human genome) can be selected to increase sensitivity.

Typically, the DNA sample is selected from the group consisting of tumor tissue, disseminated cells, feces, blood cells, blood plasma, serum, lymph nodes, urine, saliva, semen, stool, sputum, cerebrospinal fluid, tears, mucus, pancreatic juice, gastric juice, amniotic fluid, cerebrospinal fluid, serous fluids.

The present invention also relates to a method according to any of the preceding claims further comprising a step of measuring the fluorescence signals associated with the REF and MS probes, wherein: the maximal fluorescence intensity signal associated with both the REF and MS probes indicates the presence of a wild-type microsatellite sequence in the target DNA fragment, while a shift in the fluorescence intensity signal associated with the MS probe indicates the presence of a mutation in the microsatellite sequence of the target DNA fragment.

The present invention also relates to a method for the diagnostic of cancers, diseases associated with mutations in mismatch repair (MMR) genes or familial tumor predisposition in a subject, comprising the detection of a mutation in a microsatellite sequence locus of a target DNA from a DNA sample as described above, wherein the target fragment originates from a tumor.

The present invention also relates to a method for the prognosis of cancers comprising the detection of a mutation in a microsatellite sequence locus of a target fragment from a DNA sample as described above, wherein the target fragment originates from a tumor.

The present invention also relates to a method for predicting the efficacy of a treatment in a subject suffering from a cancer, comprising the detection of a mutation in a microsatellite sequence locus of a target fragment from a DNA sample as described above, wherein the target fragment is originating from a tumor and wherein the treatment is preferably immunotherapy such as immune checkpoint therapy.

The present invention also relates to a method of treatment of a cancer in a subject in need thereof comprising:

the detection of a mutation in a microsatellite sequence locus of a target fragment from a DNA sample as described above, and the administration to the subject of an immunotherapy if a mutation is identified in a microsatellite sequence locus of the target fragment, wherein the target fragment of the DNA sample originates from a tumor.

The present invention also relates to a method for the monitoring of a patient diagnosed with a tumor associated with impaired DNA mismatch repair (MMR), or having suffered from such tumor, comprising the detection of a mutation in a microsatellite sequence locus of a target fragment from a DNA sample as described above, wherein the target fragment of the DNA sample originates from a tumor.

Lastly, the present invention also encompasses a kit for identifying a mutation in a microsatellite sequence region of a target fragment from a DNA sample comprising:

a pair of primers suitable for amplifying said target fragment from the DNA sample including said microsatellites sequence;

a first oligonucleotide hydrolysis probe (MS), labeled with a first fluorophore, wherein said first oligonucleotide hydrolysis probe is complementary to a wild-type sequence including the microsatellite sequence;

a second oligonucleotide hydrolysis probe (REF), labeled with a second fluorophore, wherein said second oligonucleotide hydrolysis probe is complementary to a wild-type sequence of said amplified DNA fragment, which does not include said microsatellite sequence;

a thermostable polymerase.

DETAILED DESCRIPTION

A—Definitions

The following definitions are intended to assist in providing a clear and consistent understanding of the scope and detail of the following terms, as used to describe and define the present invention:

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein a "tumor" or a "neoplasm" (both terms can be used interchangeably) is an abnormal new growth of cells. The cells in a neoplasm usually grow more rapidly than normal cells and will continue to grow if not treated. As they grow, neoplasms can impinge upon and damage adjacent structures. The term neoplasm can refer to benign (usually curable) or malignant (cancerous) growths.

A benign tumor, or neoplasm, is usually localized, and does not spread to other parts of the body. Most benign tumors respond well to treatment. However, if left untreated, some benign tumors can grow large and lead to serious disease because of their size. Benign tumors can also mimic malignant tumors, and so for this reason are sometimes treated. Malignant tumors are cancerous growths. They are often resistant to treatment, may spread to other parts of the body (i.e. metastasis) and they sometimes recur after they were removed.

The term "cancer" is used herein for a malignant tumor.

"Allele", as used herein, refers to one of several alternative forms of a gene or DNA sequence at a specific chromosomal location (locus). At each autosomal locus an individual possesses two alleles, one inherited from the father and one from the mother.

"DNA polymorphism", as used herein, refers to the existence of two or more alleles for a given locus in the population. "Locus" or "genetic locus", as used herein, refers to a unique chromosomal location defining the position of an individual gene or DNA sequence. "Locus-specific primer", as used herein, refers to a primer that specifically hybridizes with a portion of the stated locus or its complementary strand, at least for one allele of the locus, and does not hybridize efficiently with other DNA sequences under the conditions used in the amplification method.

"Microsatellite sequence Locus" or "microsatellite sequence" are used interchangeably and refer to a region of genomic DNA that contains short, repetitive sequence elements of one (1) to seven (7), typically one (1) to five (5), notably one (1) to four (4) base pairs in length. Each sequence repeated at least once within a microsatellite locus is referred to herein as a "repeat unit". Each microsatellite locus typically includes at least seven repeat units, notably at least ten repeat units, and preferably at least twenty repeat units.

"Microsatellite Instability" (hereinafter, "MSI"), as used herein, refers to a form of genetic instability in which alleles of genomic DNA obtained from certain tissue, cells, or bodily fluids of a given subject are mutated at a microsatellite locus.

Mutations at microsatellite locus commonly typically include deletion(s), addition(s) or substitution of at least one repeat unit at a microsatellite locus. Typically, MSI results in a change in length at a microsatellite locus, due to addition(s) or most frequently deletion(s). As used herein, a "primer/probe set" refers to a grouping of a pair of oligonucleotide primers and two oligonucleotide probes that each hybridizes to a specific target nucleotide sequence. Said oligonucleotide set consists of: (a) a forward discriminatory primer that hybridizes to a first location of a nucleic acid sequence; (b) a reverse discriminatory primer that hybridizes to a second location of the nucleic acid sequence downstream of the first location and (c) two probes, which hybridizes to a target sequence between the primers. In other words, a primer/probe set consists of a pair of specific oligos that anneal to opposite strands of a nucleic acid sequence (typically including a microsatellite sequence locus) so as to form an amplicon specific to the nucleic acid sequence during the PCR reaction, and two probes, preferably fluorescent, which hybridize to (i.e., which are complementary to) a specific target sequence of the amplicon.

An "amplicon" refers to a nucleic acid fragment formed as a product of natural or artificial amplification events or techniques. Typically, the amplicon is produced by Polymerase chain reaction (PCR). "Amplifying", as used herein, refers to a process whereby multiple copies are made of one particular locus of a nucleic acid (i.e. a target sequence as mentioned above), such as genomic DNA. Amplification is accomplished using PCR (Saiki et al., 1985 Science 230: 1350-1354).

A "target (DNA) fragment", or a "target (DNA) region" used interchangeably herein relates to the fragment of the DNA sample that is amplified by a pair of primers of a primer/probe set. According to the invention, such target fragment includes a MS locus. A "target sequence", or "target DNA sequence" used interchangeably refers to a DNA sequence which is complementary to the first or the second oligonucleotide probe.

As used herein, "digital PCR" refers to an assay that provides an end-point measurement that provides the ability to quantify nucleic acids without the use of standard curves, as is used in real-time PCR (see Sykes et al., 1992 Quantitation of targets for PCR by use of limiting dilution. Bio-Techniques 13, 444-449, Vogelstein and Kinzler 1999 Digital PCR. Proc Natl Acad Sci USA, 96:9236-9241 and Pohl and Shihle 2004 Principle and applications of digital PCR. Expert Rev Mol Diagn, 4:41-47, see also Monya Baker 2012 Nature Methods 9, 541-544).

In a typical digital PCR experiment, a PCR solution is made similarly to a classical TaqMan probe assay, which typically comprises the DNA sample, fluorescence-quencher probes (i.e., hydrolysis probes), primers, and a PCR master mix, which generally contains DNA polymerase, dNTPs, $MgCl_2$, and reaction buffers at optimal concentrations. The PCR solution is then randomly distributed into discrete (i.e. individual) partitions or compartments, such that some contain no target DNA and others contain one or more target DNA copies, most preferably one target DNA copy. Thus, in these conditions, the reference signal associated with the presence of the target DNA in the DNA sample in a given partition or compartment should be theoretically 0 or 1. Obviously due to biological variability for a population of partition or compartment, clouds are observed corresponding respectively to the theoretic values 0 or 1.

The partitions are individually amplified to the terminal plateau phase of PCR (or end-point) and then read for fluorescence, to determine the fraction of positive partitions.

If the partitions are of uniform volume, the number of target DNA molecules present may be calculated from the fraction of positive end-point reactions using Poisson statistics, according to the following equation:

$$\lambda = \ln(1-p) \qquad (1)$$

wherein $\lambda$ is the average number of target DNA molecules per replicate reaction and p is the fraction of positive end-point reactions. From $\lambda$, together with the volume of each replicate PCR and the total number of replicates analyzed, an estimate of the absolute target DNA concentration is calculated.

Micro well plates, capillaries, oil emulsion, and arrays of miniaturized chambers with nucleic acid binding surfaces can be used to partition the samples in distinct compartments or droplets. Thus digital PCR as used herein includes a variety of formats, including droplet digital PCR (ddPCR), BEAMing (beads, emulsion, amplification, and magnetic), and microfluidic chips.

"Droplet digital PCR" (ddPCR) refers to a digital PCR assay that measures absolute quantities by counting nucleic acid molecules encapsulated in discrete, volumetrically defined, water-in-oil droplet partitions that support PCR amplification (Hinson et al., 2011, Anal. Chem. 83:8604-8610; Pinheiro et al., 2012, Anal. Chem. 84: 1003-1011). A single ddPCR reaction may be comprised of at least 20,000 partitioned droplets per well.

A "droplet" refers to an individual partition of the PCR solution in a droplet digital PCR assay. In the following of the present application, digital PCR will be described in reference to droplet digital (or digital droplet PCR, used interchangeably), however, as mentioned previously individual partition of the PCR solution according to the principle of digital PCR can be obtained according to a variety of techniques. Therefore, the method of the invention as described below in reference to droplet digital PCR is not limited to this digital PCR technique and may be applied in a similar fashion to other digital PCR techniques.

Techniques available for digital PCR include PCR amplification on a microfluidic chip (Warren et al., 2006 Transcription factor profiling in individual hematopoietic progenitors by digital RT-PCR. Proc Natl Acad Sci USA 103, 17807-17812; Ottesen et al., 2006 Microfluidic digital PCR enables multigene analysis of individual environmental bacteria. Science 314, 1464-1467; Fan and Quake 2007 Detection of aneuploidy with digital polymerase chain reaction. Anal Chem 79, 7576-7579). Other systems involve separation onto microarrays (Morrison et al., 2006 Nanoliter high-throughput quantitative PCR. Nucleic Acids Res 34, e123) or spinning microfluidic discs (Sundberg et al., 2010 Spinning disk platform for microfluidic digital polymerase chain reaction. Anal Chem 82, 1546-1550) and droplet techniques based on oil-water emulsions (Hindson, Benjamin et al., 2011 High-Throughput Droplet Digital PCR System for Absolute Quantitation of DNA Copy Number. Analytical Chemistry 83 (22): 8604-8610). Typically, digital PCR is selected from droplet digital PCR (ddPCR), BEAMing (beads, emulsion, amplification, and magnetic), and microfluidic chips. Preferably, the digital PCR is droplet digital PCR.

A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84: 1003-1011). Once droplets are generated, they can be transferred on a PCR plate and emulsified PCR reactions can be run on a thermal cycler under a classical program such as for example described in the Biorad's Guideline for ddPCR (http://www.bio-rad.com/webroot/web/pdf/lsr/literature/Bulletin_6407.pdf).

Droplet digital PCR may be performed using any platform that performs a digital PCR assay that measures absolute quantities by counting nucleic acid molecules encapsulated in discrete, volumetrically defined, water-in-oil droplet partitions that support PCR amplification. The strategy for droplet digital PCR may be summarized as follows: The PCR solution containing the DNA sample is diluted and partitioned into thousands to millions of separate reaction chambers (water-in-oil droplets) so that each contains one or no copies of the nucleic acid molecule of interest.

The number of "positive" droplets detected, which contain the target amplicon (i.e., target DNA fragment) (i.e., according to the present invention REF positive droplets), versus the number of "negative" droplets, which do not contain the target amplicon (i.e., REF negative droplets), may be used to determine the number of copies of the nucleic acid molecule of interest that were in the original sample.

Examples of droplet digital PCR systems include the QX100™ Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000,000 to 10,000,000 picoliter-sized droplets.

The benefits of dPCR and more particularly ddPCR technology include:

Absolute quantification, as ddPCR technology provides an absolute count of target DNA copies per input sample without the need for running standard curves.

Unparalleled precision, as the massive sample partitioning afforded by ddPCR enables the reliable measurement of small fold differences in target DNA sequence copy numbers among samples.

Increased signal-to-noise ratio: high-copy templates and background are diluted, effectively enriching template concentration in target-positive partitions, allowing for the sensitive detection of rare targets.

Removal of PCR bias, as error rates are reduced by removing the amplification efficiency reliance of qPCR, enabling the detection of small (1.2-fold) differences.

Simplified quantification, since neither calibration standards nor a reference required for absolute quantification.

Reduced consumable costs, as reaction volumes are in the pico- to nanoliter ranges, reducing reagent use and the sample quantity required for each data point.

Lower equipment costs, as the emulsion-based reaction system means that the PCR reactions can be performed in a standard thermal cycler without complex chips or microfluidics.

Superior partitioning, since ddPCR technology yields 20,000 droplets per 20 µl sample, nearly two million partitioned PCR reactions in a 96-well plate, whereas chip-based digital PCR systems produce only hundreds or thousands of partitions. The greater number of partitions also yields higher accuracy.

The term "melting temperature" or "Tm" refers to the temperature at which a polynucleotide dissociates from its complementary sequence. Generally the Tm may be defined as the temperature at which one-half of the Watson-Crick base pairs in a duplex nucleic acid molecule are broken or dissociated (i.e. are "melted") while the other half of the Watson-Crick base pair remain intact in a double stranded conformation. In other words, the Tm is defined as the temperature at which 50% of the nucleotides of two complementary sequences are annealed (double strands) and 50% of the nucleotides are denatures (single strands). The Tm can be estimated by a number of methods, such as for example by a nearest-neighbor calculation as per Wetmur 1991 (Wetmur 1991 DNA probes: applications of the principles of nucleic acid hybridization. Crit Rev Biochem Mol Biol 26: 227-259, hereby incorporated by reference) or by commercial programs including Oligo™ Primer Design and programs available on the internet. Alternatively, the Tm can be determined through actual experimentation. For example, double-stranded DNA binding or intercalating dyes, such as ethidium bromide or SYBR-green (Molecular Probes) can be used in a melting curve assay to determine the actual Tm of the nucleic acid.

As used herein, the term "critical denaturation temperature" or "Tc" refers to a temperature below the Tm of the wild type sequence, at which temperature a duplex of the wild-type sequence and the mutant sequence will melt. (In some instances, this temperature may be one at which a homoduplex of the mutant sequences also melts). The critical denaturing temperature (Tc) is the temperature below which PCR efficiency drops abruptly for a given nucleic acid sequence.

B—Method for Identifying a Mutation in a Microsatellite Sequence Locus of a DNA Sample The present invention relates to a method for the detection of a mutation in a target microsatellite sequence (MS) locus of target fragment from a DNA sample, comprising a step of subjecting said DNA sample to a polymerase chain reaction (PCR) in the presence of:
- a pair of primers suitable for amplifying said target fragment of the DNA sample including the said MS locus;
- a first MS oligonucleotide probe, labeled with a first fluorophore, wherein said first MS oligonucleotide probe is complementary to a first wild-type target sequence including the microsatellite sequence;
- a second oligonucleotide reference (REF) probe, labeled with a second fluorophore, wherein said second oligonucleotide REF probe is complementary to a second wild-type target sequence of said amplified DNA fragment which does not include the said microsatellite sequence.

The DNA from the DNA sample and in particular the target DNA (or target DNA fragment), can be genomic DNA or DNA issued from reverse RNA transcription. The genomic DNA may be constitutional DNA, DNA originating from a tumor (i.e. tumor genomic DNA), notably a malignant tumor. Typically also, the target DNA fragment is cell-free DNA, such as circulating DNA. In particular, the target DNA fragment can be cell-free tumor DNA, notably circulating tumor DNA, or cell-free fetal DNA (i.e., fetal DNA circulating in the maternal blood stream).

The method uses a primer/probe set as previously defined.

Preferably, the primer pair is typically designed so as to have a Tm lower than the Tc of the reaction. The pair of primer can be designed using available computer programs. Typically, the probes according to the invention are hydrolysis probes (also named TaqMan probes). Hydrolysis probes have a fluorophore covalently attached to their 5'-end of the oligonucleotide probe and a quencher.

Oligonucleotide probes are detectably labeled with a fluorescent label which can be selected, for example, from the group consisting of FAM (5- or 6-carboxyfluorescein), VIC, NED, Fluorescein, FITC, IRD-700/800, CY3, CY5, CY3.5, CY5.5, HEX, TET (5-tetrachloro-fluorescein), TAMRA, JOE, ROX, BODIPY TMR, Oregon Green, Rhodamine Green, Rhodamine Red, Texas Red, Yakima Yellow, Alexa Fluor PET, Biosearch Blue™, Marina Blue®, Bothell Blue®, Alexa Fluor®, 350 FAM™, SYBR® Green 1, Fluorescein, EvaGreen™, Alexa Fluor® 488 JOE™, 25 VIC™, HEX™, TET™, CAL Fluor® Gold 540, Yakima Yellow®, ROX™, CAL Fluor® Red 610, Cy3.5™, Texas Red®, Alexa Fluor® 568 Cry5 ™, Quasar™ 670, LightCycler Red640®, Alexa Fluor 633 Quasar™ 705, LightCycler Red705®, Alexa Fluor® 680, SYT0® 9, LC Green®, LC Green® Plus+, and EvaGreen™. Preferably, the detectable label is selected from 6-carboxyfluorescein, FAM, or tetrachlorofluorescein, (acronym: TET), Texas Red, Cyanin 5, Cyanine 3, or VIC™.

The quencher may be an internal quencher or a quencher located in the 3' end of the probe. Typical quenchers are tetramethylrhodamine, TAMRA, Black Hole Quencher or nonfluorescent quencher. Hydrolysis probes usable according to the invention are well-known in the field (see notably http://www.sigmaaldrich.com/technical-documents/articles/biology/quantitative-pcr-and-digital-pcr-detection-methods.html). The quencher molecule quenches the fluorescence emitted by the fluorophore when excited by the cycler's light source typically via FRET (Förster Resonance Energy Transfer). As long as the fluorophore and the quencher are in proximity, quenching inhibits any fluorescence signals. Such probes are designed such that they anneal within the target region amplified by a specific set of primers. As the Taq polymerase extends the primer and synthesizes the nascent strand, the 5'-3' exonuclease activity inherent in the Taq DNA polymerase then separates the 5' reporter from the 3' quencher, which provides a fluorescent signal that is proportional to the amplicon yield.

The first and second probes according to the invention are located within the same amplicon. The probes are designed according to the well-established practice in the art to preferably minimize PCR artifact and to specifically hybridize with the sequences as defined below. The first and second probes are labeled with distinct fluorophores in order to allow separate detection of their respective signal.

In some embodiments, the hydrolysis probes according to the invention include a minor groove binder (MGB) moiety at their 3' end. Such MGB typically increases the melting temperature (Tm) of the probe and stabilizes probe-target hybrids.

The oligonucleotide probes have a nucleotide sequence length of about 10 to about 50. Preferably, the oligonucleotide probes (and in particular the MS probe) have a nucleotide sequence length of about 15 to 40, or 25 to 50 or notably 15 to 35.

Preferably, the oligonucleotide probes (and in particular the MS probe) have a nucleotide sequence length of about 20 to 40, or 30 to 50 or notably 30 to 40.

The first probe according to the invention (also named MS probe) hybridizes with a first wild-type target sequence of the amplified target DNA fragment, which includes a microsatellite sequence locus. Preferably the probe covers the full wild-type microsatellite sequence and extends further a few nucleotides on each extremity (typically 1 to 10 nucleotides, notably 2 to 8, preferably 2 to 6, most preferably 2 to 5 or 2 to 4) to confer both its ability to bind properly and the resulting destabilization in case of microsatellite instability. In other words, the probe size is designed to confer its ability to bind properly to the wild-type microsatellite sequence, while preventing hybridization of the MS probes in the presence of a mutation in the microsatellite sequence.

The second probe of the invention (also named REF probe) hybridizes with a second wild-type target sequence of said amplified DNA fragment, which does not include the said microsatellite sequence. In particular, said second probe may partially overlap with the said microsatellite sequence or be located outside of the said microsatellite sequence. Preferably the second probe according to the invention is located outside of the said microsatellite sequence.

Various microsatellite sequence loci can be targeted in the first wild-type target sequence according to the invention. Microsatellite sequence loci or markers than can be targeted according to the invention are notably described in Bacher et al., 2004 Disease Markers 20, 237-250, as well as in Hause et al., 2016 Nat Medicine November 22(11):1342-1350). Preferably, targeted microsatellite sequence loci (or microsatellite markers) are selected from microsatellites found to be highly associated with MSI positive tumors, based on their frequency of instability in colon, endometrial, rectal and stomach adenocarcinomas. Preferably, targeted microsatellite sequence loci are located in regions frequently amplified in tumors.

For example, a targeted microsatellite sequence locus can be selected from BAT-25, BAT-26, BAT-34c4, BAT-40, NR21, NR24, MONO-27, D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1.

In one embodiment, the target microsatellite sequence locus may also be selected among the Bethesda panel, which comprises BAT-25, BAT-26, D2S123, D5S346 and D17S250.

Mononucleotide repeat loci have been shown to be very susceptible to alteration in tumors with dysfunctional DNA mismatch repair systems (Parsons, 1995 supra), making such loci particularly useful for the detection of cancer and other diseases associated with dysfunctional DNA mismatch repair systems, such that mononucleotides MSI markers may be preferred.

In one embodiment of the invention, a targeted microsatellite sequence locus is BAT-26 and/or ACVR2A and/or DEFB105A and DEFB105B.

More generally, appropriate microsatellite sequence loci that can be targeted according to the invention are short microsatellite sequences (typically comprising 8 to 30, notably 8 to 25, preferably, 8 to 20, most preferably 8 to 15 or 8 to 12 nucleotides) such as the target microsatellite sequence locus exemplified in the group consisting of D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1.

Depending on the microsatellite locus, probes of various sizes and G/C content may also be used. For example, probes of more than 30 nucleotides and/or with a G/C content of less than 30% may be used. This is notably the case with BAT-26. As a matter of example an MS probe of SEQ ID No.:4, which hybridize with a sequence including the BAT-26 microsatellite sequence can be used. Primers of sequences SEQ ID No: 1-2 as well as REF probe and MS probe of respectively SEQ ID No: 3 and 4 represent an illustrative set of primer/probe that can be used according to the invention.

According to the present invention, amplification of the target DNA fragment occurs with a digital PCR technique. Typically, in such a technique, the PCR solution is divided in multiple compartments or droplets, which are made to run PCR individually. Typically also most of the compartments or droplets contain either 0 or 1 copy of the target DNA fragment which is to be amplified.

To circumvent the technical challenges associated to the amplification of low complexity sequence such as the microsatellite sequence, a series of modifications may be provided to Biorad's Guideline for ddPCR as mentioned above, in order to achieve proper hybridization of the MS probe to WT alleles. Reaction annealing temperature and/or extension time may be increased. Typical annealing temperature according to Biorad's Guidelines is 55° C. Said annealing temperature may be advantageously increased from 3 to 15° C.

Thermal cycling is performed to endpoint. Thus after multiple PCR amplification cycles (i.e. after completing PCR cycles), the raw PCR data are then collected by measuring the fluorescence signal associated with both the REF and MS probes for each droplet. Droplets containing WT target fragments display a double positive fluorescence signal coming from the hybridization of both the REF and MS probes (REF+/MS+ droplets). The non-hybridization (or inefficient hybridization) of the MS probe in droplets containing mutated microsatellite alleles leads to a shift of the droplet cloud on the 2D graph, toward a single REF positive (REF+) population, which is proportional to the fraction of droplets containing mutant microsatellite alleles.

Typically, raw dPCR (or ddPCR) data are collected after PCR cycling by reading or measuring the fluorescence signal associated with the REF and MS probes for each droplet.

The PCR data collection step is typically performed in an optical detector (for example the Bio-Rad QX-100 droplet reader can be used in ddPCR). Preferably at least a two-color detection system is used (for example to detect FAM and either HEX or VIC fluorescent labels). Droplets clouds can typically be established on 2D graphs by plotting the fluorescence level for each probe per droplet. In some embodiments, analysis may be achieved with appropriate software (such as the QuantaSoft v1.7.4 software for ddPCR or the package on ddPCR R [https://cran.r-project.org/web/packages/ddpcr/index.html]. Quantasoft allows manual assignment of the droplets to the single REF positive or the double REF/MS positive population (i.e. or clouds). The R package defines thresholds in an automatic way to avoid bias that might be introduced by manual assignment.

The number of droplets that are positive for the reference probe (REF probe) can be used to quantify the total number of target DNA fragments in the sample. The fraction of positive droplets can then be fitted to a Poisson distribution to determine the absolute initial copy number of the target DNA fragment in the input reaction mixture in units of copies/µl.

In droplets containing a wild-type target DNA (no mutation in the targeted MS sequence), a maximum fluorescence signal is observed for both the REF and the MS probes. At the contrary, in droplets containing a mutated sequence in the amplified target DNA fragment (i.e. a mutation in the microsatellite sequence), a shift in the fluorescence intensity is observed for the signal associated with the MS probe.

Most preferably, the digital PCR reaction is designed to ensure that most droplets contain either 0 or 1 copy of targeted DNA fragment (notably depending on the quantity of DNA loaded in the reaction. In these conditions, an optimal separation of the WT (REF+/MS+ signals) vs. mutated microsatellite (or MSI) clouds (single REF+signal) can be observed. It must be noted that due to biological variability that droplets classified in the single REF+ signal may include a residual (i.e., non-significant) MS signal. A threshold, under which a MS signal is considered as "a residual MS signal" can be determined by the one skilled in the art according to classical signal analysis techniques. Said threshold can be typically set using the R package as mentioned previously.

Typically mutant allele frequency can be determined from droplet counts through manual assignment of WT and mutated microsatellite droplet clouds. As mentioned above, identification of a droplet population with a single signal from the REF probe indicates the presence of a mutated microsatellite sequence in the DNA sample.

Mutant allele frequency which can be determined as mentioned above can be compared with a control mutated allele frequency obtained from a control DNA sample. The control DNA sample may be a wild-type sample or a sample or cell line collected in a subject, diagnosed with a MSI positive tumor or with a disease associated with a mutation in the DNA mismatch repair, at a prior time point, during the time-course of the disease and/or during the time course of the treatment.

As used herein, the term "sample" refers to anything which may contain DNA and notably the DNA fragment to be amplified. In some embodiment, the "sample" contains RNA and is therefore submitted to a reverse transcription step. The sample may be a biological sample, such as a biological fluid or a biological tissue. Examples of biological fluids include urine, blood, plasma, serum, saliva, semen, stool, sputum, cerebrospinal fluid, tears, mucus, pancreatic juice, gastric juice amniotic fluid, serous fluids such as pericardial fluid, pleural fluid or peritoneal fluid.

Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumor tissue, lymph nodes, arteries and disseminated cell(s). The tissue can be fresh, freshly frozen, or fixed, such as formalin-fixed paraffin-embedded (FFPE) tissues. The sample can be obtained by any means, for example via a surgical procedure, such as a biopsy, or by a less invasive method, including, but not limited to, abrasion or fine needle aspiration. Preferably, the DNA sample is selected from the group consisting of: tumor tissue, disseminated cells, feces, blood cells, blood plasma, serum, lymph nodes, urine, saliva, semen, stool, sputum, cerebrospinal fluid, tears, mucus, pancreatic juice, gastric juice, amniotic fluid, cerebrospinal fluid, serous fluids such as pericardial fluid, pleural fluid or peritoneal fluid.

The DNA and notably the target DNA fragment can be genomic DNA or DNA issued from reverse transcriptase. The genomic DNA can be constitutional DNA, tumor DNA or fetal DNA. In some embodiments, notably when the sample is a biological fluid, the DNA sample may contain cell-free DNA (cfDNA), or circulating DNA. Early studies have shown that tumor DNA is released into the circulation, and is present in particularly high concentrations in plasma and serum in a number of different types of cancer (Leon et al., 1977 Cancer Res 37:646-650; Stroun et al., 1989 Oncology 46:318-322). Thus, DNA sample according to the invention can contain cell-free tumor DNA or circulating tumor DNA. In another embodiment, the DNA sample contains cell-free fetal DNA. Due to its high sensitivity, the method of the invention can be used on plasma sample containing low concentration of circulating, or cell-free target DNA such as cell-free or circulating tumor DNA or fetal DNA. In some embodiments of the present invention, the DNA can be obtained from reverse transcription of an RNA sample.

Typically a DNA sample according to the invention is obtained from a subject. The subject, or the patient (both terms can be used interchangeably) of the invention is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

In some embodiments of the invention, the subject has a cancer, is in remission of a cancer, or is at risk of suffering from a cancer notably based on family history. In some embodiments for example the subject has familial tumor predisposition.

In some embodiment, the subject is suffering from, is in remission, or has familial cancer predisposition, notably the subject is suffering from or is at risk of suffering from a disease caused by mutations in mismatch repair (MMR) genes, such as Constitutional mismatch repair deficiency syndrome (CMMRD syndrome) or Lynch syndrome.

The cancer may be a solid cancer or a "liquid tumor" such as cancers affecting the blood, bone marrow and lymphoid system, also known as tumors of the hematopoietic and lymphoid tissues, which notably include leukemia and lymphoma. Liquid tumors include for example acute myelogenous leukemia (AML), chronic myelogenous leukemia (CML), acute lymphocytic leukemia (ALL), and chronic lymphocytic leukemia (CLL), (including various lymphomas such as mantle cell lymphoma or non-Hodgkins lymphoma (NHL). Solid cancers notably include cancers affecting one of the organs selected from the group consisting of: colon, rectum, skin, endometrium, lung (including non-small cell lung carcinoma), uterus, bones (such as Osteosarcoma, Chondrosarcomas, Ewing's sarcoma, Fibrosarcomas, Giant cell tumors, Adamantinomas, and Chordomas), liver, kidney, esophagus, stomach, bladder, pancreas, cervix, brain (such as Meningiomas, Glioblastomas, Lower-Grade Astrocytomas, Oligodendrocytomas, Pituitary Tumors, Schwannomas, and Metastatic brain cancers), ovary, breast, head and neck region, testis, prostate and the thyroid gland.

In some embodiments of the present invention the cancer is the Constitutional mismatch repair deficiency syndrome (CMMRD syndrome) or the Lynch syndrome In the context of the present invention, a cancer (or a tumor) associated with MSI is also named a MSI positive cancer (or a MSI positive tumor) and relates to a cancer (or tumor) wherein the genomic tumor DNA exhibits at least one mutation in a microsatellite sequence. A MSI positive cancer may thus be any of the cancers as listed above wherein the genomic tumor DNA exhibits at least one mutation in a microsatellite sequence Clinical Applications: Diagnostic and Prognosis Methods, Therapeutic Treatment and Patient Monitoring The method for identifying a mutated microsatellite sequence in a target DNA fragment as described above has several major and direct clinical applications.

First, as previously mentioned, microsatellite instability is a hypermutator phenotype that occurs in tumors associated with impaired DNA mismatch repair (MMR). MSI has thus been associated with a great variety of cancers such as but not limited to colorectal cancers, gastric cancer, endometrium cancer, ovarian cancer, urinary tract cancer, brain cancer, and breast cancer. MSI is most prevalent as the consequence of colon cancers. MSI is typically found the Constitutional mismatch repair deficiency syndrome (CMMRD syndrome) or the Lynch syndrome.

Therefore, detection of a mutated microsatellite sequence according to the method as previously described can be used in the diagnostic of cancers as previously defined, in particular of cancers (as previously defined), which are associated with impaired DNA mismatch repair and notably of MSI positive cancers (or tumors).

In one embodiment of the invention, detection of a mutated microsatellite sequence according to the method can also be used in the diagnostic of diseases which are caused by mutations in mismatch repair (MMR) genes, such MSI positive tumors notably such as Constitutional mismatch repair deficiency syndrome (CMMRD syndrome) or Lynch syndrome, or in the diagnostic of familial tumor predisposition in a subject.

Thus in one aspect, the present invention relates to a method for the diagnostic of cancers, notably of diseases associated with mutations in mismatch repair (MMR) genes, such as MSI positive tumors, and/or of familial tumor predisposition to cancer in a subject, comprising the detection of a mutation in a microsatellite sequence locus of a target DNA from a DNA sample according to the present invention. Typically the target DNA is genomic DNA originating from a tumor. The sample can be obtained from a subject as previously described. In one embodiment, detection of a mutated microsatellite sequence in a DNA sample from a subject indicates that the subject is suffering from a disease caused by mutations in the MMR genes such as MSI positive tumors, notably CMMRD or Lynch syndrome. Detection of a mutated microsatellite sequence in a DNA sample from a subject may also indicate that the subject has familial tumor predisposition such as in the CMMRD or Lynch syndrome.

Mutations in MMR genes include addition, deletion or substitution, in particular single nucleotide variations (SNVs), as well as epimutations (such as DNA hypermethylation).

The prevalence of MSI positive tumors is higher in colorectal cancers, gastric cancers, endometrium cancers. However, MSI has been found at a lower prevalence in virtually all type of cancers (see Hause et al., 2016 Nature Medicine), albeit with low prevalence. As previously mentioned, the MSI phenotype of the cancer (i.e. positive or negative) has important implications in cancer prognosis and rational planning of treatment (Boland and Goel, Gastroenterology 2010). Therefore even in the case of cancers with low MSI positive prevalence, it remains of high relevance to identify whether the patient is suffering from a MSI positive tumor or a MSI negative tumor. The method of the present invention can therefore be used in the prognosis of various cancers. Identification of a positive MSI cancer is generally associated with a better prognosis.

Thus, the present invention also relates to a method for the prognosis of cancers (as previously defined) comprising the detection of a mutation in a microsatellite sequence locus of a DNA sample according to the present invention. In some embodiment, identification of a mutated microsatellite sequence in the sample, preferably a DNA sample originating from a tumor, indicates that said tumor is MSI positive.

In the therapeutic contexts as above mentioned, the methods of the invention are particularly useful as its great sensitivity allows detection of microsatellite instability in DNA samples containing very low concentrations of target DNA. The method of the invention can therefore be routinely performed on biological samples such as blood samples, plasma samples, urine or even feces. Typically, the methods of the invention are performed on blood sample or plasma sample and the target DNA is a cell-free DNA, such as a circulating tumor DNA. This point is particularly relevant for diseases such as CMMRD, which involve cerebral tumor with no biopsy access.

The present invention also relates to a method for predicting the efficacy of a treatment, as reports have shown for example that colorectal cancer patients with MMR deficiency have better responses to immunotherapy by PD-1 immune checkpoint blockade and show improved progression-free survival. Therefore, identification of patients suffering from cancer associated with MSI (i.e. MSI positive cancer or tumor) is of high clinical relevance for selection of an appropriate therapeutic strategy.

Thus, another aspect of the present invention concerns a method for predicting the efficacy of a treatment in a subject suffering from a cancer, wherein said method comprises the detection of a mutation in a microsatellite sequence locus of a target DNA fragment from a subject DNA sample as previously described. Preferably, the target DNA fragment is originating from a tumor. Typically the DNA sample is obtained from a subject suffering from a tumor and/or having familial cancer predisposition.

The present invention also proposes a method of treatment of a cancer in a subject in need thereof comprising the detection of a mutation in a microsatellite sequence locus of a target DNA fragment from a DNA sample according to the methods as herein described. Typically the target DNA fragment is originating from a tumor. Typically also the DNA sample is obtained from a subject suffering from a tumor and/or having familial cancer predisposition.

Preferably, the treatment is immunotherapy. Immunotherapy includes but is not limited to immune checkpoint modulators (i.e. inhibitors and/or agonists), monoclonal antibodies, cancer vaccines.

Most preferably, the treatment comprises administration of immune checkpoint modulators such as anti-PD-1 and/or anti-PDL-1 inhibitors.

Preferably, immunotherapy is administered to the subject if a mutation in a microsatellite sequence locus of a target DNA (notably a target tumor DNA) from a DNA sample is detected.

Furthermore, the method of the invention for detecting microsatellite instability may also be used for the monitoring of a subject diagnosed with a tumor associated with impaired DNA mismatch repair. Preferably, said monitoring is performed during the time course of the treatment. The method may also be used for the monitoring of cancer relapse in a subject having suffered from a tumor associated with impaired DNA mismatch repair. Thus, in another aspect, the present invention also provides a method for the monitoring of a patient diagnosed with a tumor associated with impaired DNA mismatch repair, or having suffered from such a tumor, comprising the detection of a mutation in a microsatellite sequence locus of a target tumor DNA from a DNA sample selected from a plasma or a serum sample obtained from a subject diagnosed with a tumor associated with impaired DNA mismatch repair or having suffered from a tumor associated with impaired DNA mismatch repair. In patient having suffered from a tumor associated with impaired DNA mismatch repair, detection of microsatellite instability in circulating tumor DNA may be indicative of a relapse.

Multiplexed Assays for the Detection of a Mutation in a Microsatellite Sequence Locus of a Target DNA from a DNA Sample The power for detecting the presence of MSI in tissues associated with a particular disease, such as cancerous tumors, can be increased tremendously by multiplexing multiple markers. Thus, in the context of the invention more than one set of primer/probe as previously defined can be used in a multiplexed assay such that more than one microsatellite sequence locus (i.e.; a panel microsatellite sequence loci) as previously defined can be targeted.

As a matter of example, microsatellite sequence loci of the panel for multiplexed assays according to the invention can be selected among the group consisting of BAT-25, BAT-26, BAT-34c4, BAT-40, NR21, NR24, MONO-27, D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1 and in any of the groups as previously defined.

Such multiplexed assay is particularly useful in the clinical applications as previously described.

Preferably, in multiplexed assays, the primers pairs are designed using available computer programs such that upon amplification the resulting amplicons are predicted to have the same melting temperature.

When in the digital range (where all compartments contain either 0 or 1 target molecule) it is possible to multiplex qPCR assays without concern for competition or cross reactivity, as each target-containing reaction will proceed with the target binding to its primers/probe specifically, whereas no reaction will occur in compartments without targets. Having each molecule in a separate reaction compartment allows both high and low abundance targets to be counted in the same experiment without concern for "swamping out" the low abundance target (since each compartment has at most 1 target, independent of its concentration in the average sample volume). When more than one target is counted (e.g., in a duplex assay format), ratios of the counts for one target relative to another (e.g., mutant allele vs. wild type allele) enable "absolute ratios" to be quantified, using one of the targets as an internal normalizing reference (e.g., how many amplifiable genome equivalents were loaded) that has gone through the identical experiment as the other targets assayed.

In addition, since dPCR is performed as an endpoint reaction (PCR is run to completion before measuring fluorescence), having true single target molecules in isolation allows multiplexing based on probe intensity (Zhong, Bhattacharya, et al., 2011 Multiplex digital PCR: breaking the one target per color barrier of quantitative PCR. Lab Chip, 11:2167-2174). By adding the target-specific fluorescent assay at a limiting concentration, a compartment with that target molecule will be PCR-positive, but with a limited brightness at PCR endpoint. To count a second target type, a different target-specific probe with the same "color" (i.e. with the same fluorophore) is added at a different concentration. A compartment with the second target will have a brighter signal at PCR endpoint than a compartment with the first target, providing separate clouds and thus enabling separate counts for each target. Thus, combinations of both different color probes and different concentration probes can be used to multiplex at higher levels.

Kits

The present invention also encompasses kit for identifying a mutation in a microsatellite sequence region of a DNA sample comprising a primer/probe set comprising:
- a pair of primers suitable for amplifying a target DNA fragment of said DNA sample including the said microsatellites sequence;
- a first oligonucleotide probe, labeled with a first fluorophore, wherein said first oligonucleotide probe is complementary to a wild-type sequence including the microsatellites sequence;
- a second oligonucleotide probe, labeled with a second fluorophore, wherein said second oligonucleotide probe is complementary to a wild-type sequence of said amplified DNA fragment located outside of the said microsatellite sequence;
- a thermostable DNA polymerase.

Thermostable DNA polymerases are typically described in Newton and Graham 1994 In: PCR, BIOS Scientific Publishers, Ltd., Oxford, UK. 13. Advantageously, the thermostable polymerase is the Taq polymerase.

In one aspect, the kit comprises more than one primer/probe set, wherein the primer/probe sets allows amplification and detection of target DNA fragments comprising distinct microsatellite sequences.

The kit as above mentioned can be used in the clinical applications as previously described.

FIGURES

FIG. 1: A-C. 2-D fluorescence amplitude scatter plots of BAT-26 ddPCR MSI assay using HCT-116 cell line DNA (MSI-H), PBMC (WT) or a 10% dilution of HCT-116 in WT DNA. D-F. 2-D fluorescence amplitude scatter plots of DEFB105A/B ddPCR MSI assay using HCT-116 cell line DNA (MSI-H), PBMC (WT) or a 10% dilution of HCT-116 in WT DNA. G-I. 2-D fluorescence amplitude scatter plots of ACVR2A ddPCR MSI assay using HCT-116 cell line DNA (MSI-H), PBMC (WT) or a 10% dilution of HCT-116 in WT DNA. Droplets containing WT alleles are positive for both FAM and VIC signals, while droplets containing MSI alleles are positives for VIC signal only.

Figure 2:
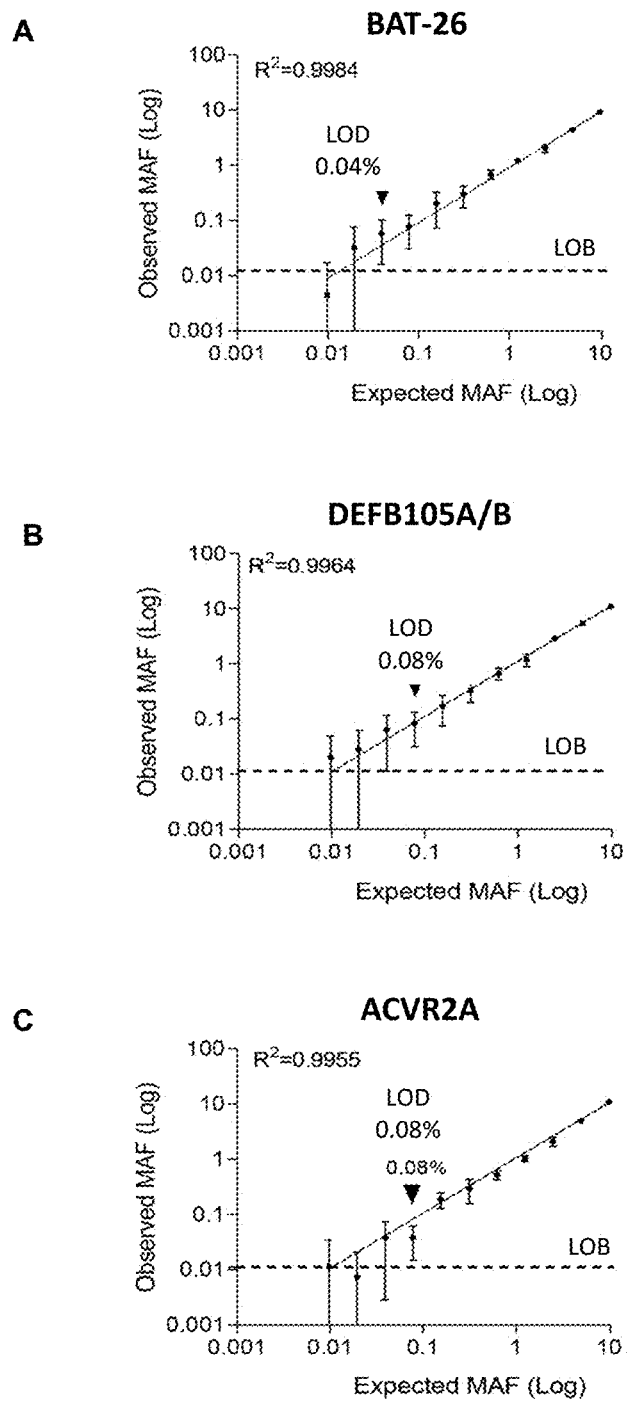

FIG. 2: Correlation curves obtained for BAT-26 (A), DEFB105A/B (B) and ACVR2A (C) assays for observed versus expected MAFs in reconstituted mutant serial dilutions (10%, 5%, 2.5%, 1.25, 0.63%, 0.31%, 0.16%, 0.08%, 0.04%, 0.02%, 0.01%). Dotted lines: LOB, estimated as the upper 95% CI of false-positive calls in at least 53 independent ddPCR reactions with WT DNA.

Figure 3:
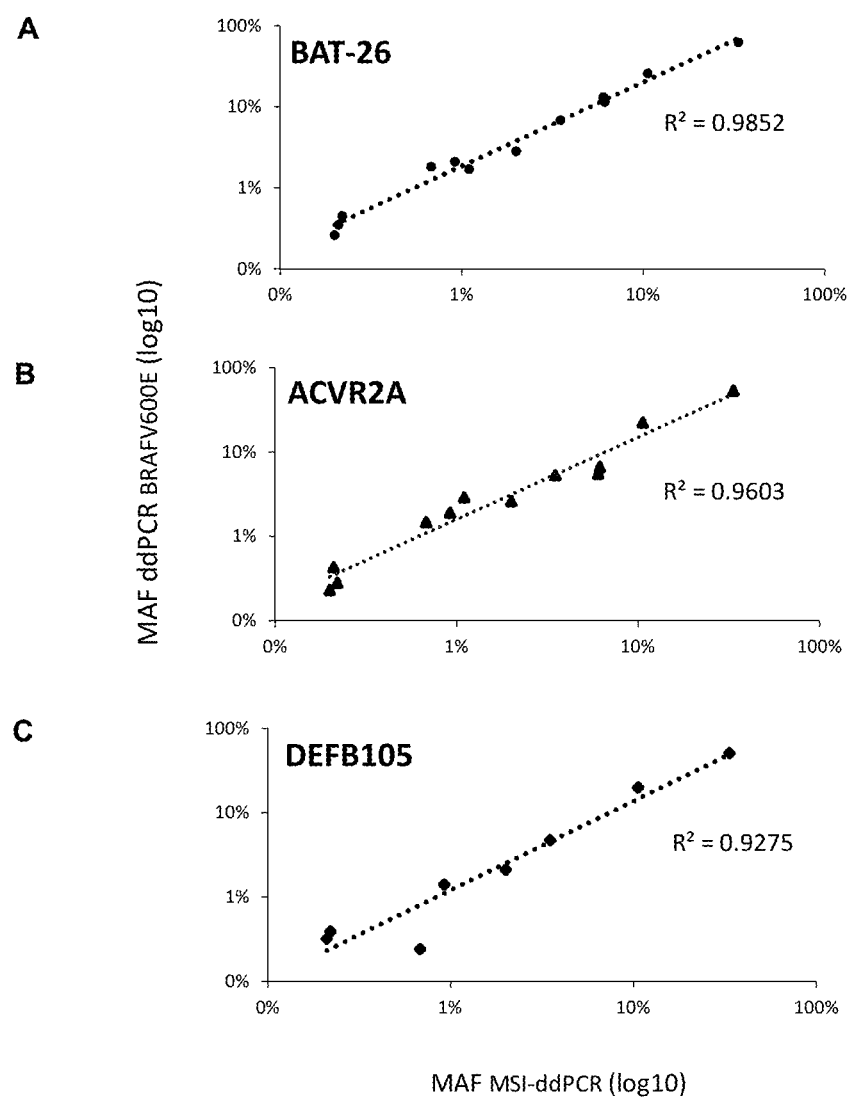

FIG. 3: Correlation between ctDNA fractions estimated by BAT-26 (A), ACVR2A (B) or DEFB105A/B (C) ddPCR assays and a ddPCR assay targeting specifically BRAF$^{V600E}$ mutation.

Figure 4:
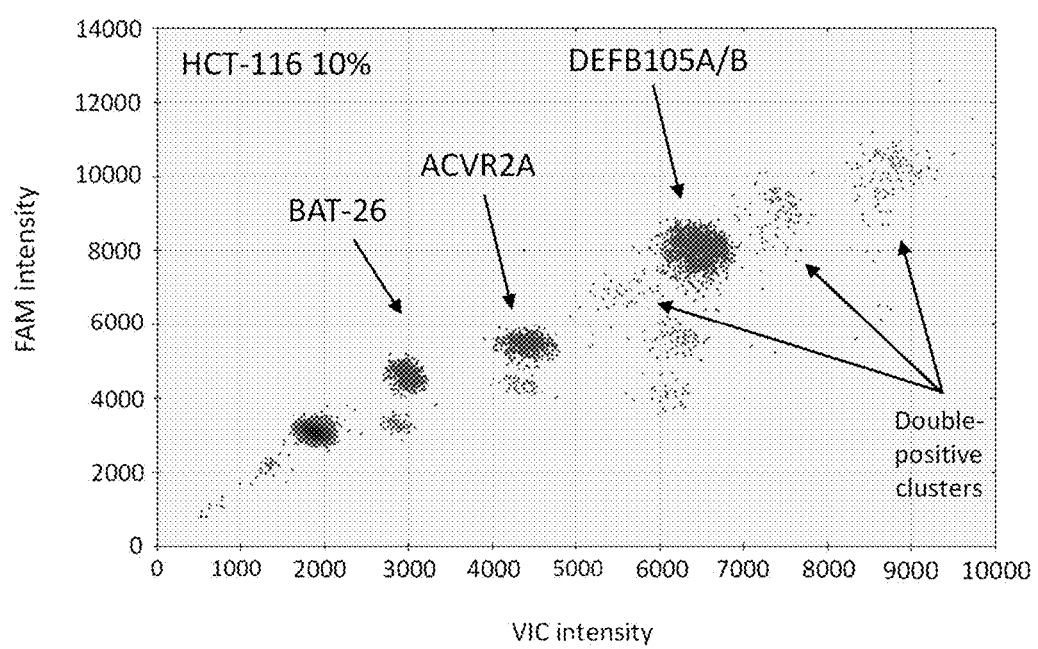

FIG. 4: 2-D fluorescence amplitude scatter plot illustrating fluorescence signals obtained with a triplex assay targeting simultaneously BAT-26, ACVR2A and DEFB105A/B microsatellite markers using a 10% dilution of HCT-116 cell line in WT DNA. Results obtained with annealing temperature and extension time at 63° C. for 3 min. Primers and probes concentrations were: BAT-26: 0.2×; ACVR2A: 0.6×; DEFB105A/B: 1×.

RESULTS

Material and Methods

Primers and Probe Design

Primers and probes were designed with the support of Primer3Plus Software (Whitehead Institute for Biomedical Research). All primers were checked for non-specific binding using Primer BLAST and absence of secondary structures. Primers were designed to generate amplicons smaller than 140 bp for optimal amplification of cell free DNA (cfDNA) and fragmented DNA extracted from formalin-fixed paraffin-embedded (FFPE) tumor samples. Oligonucleotide sequences used in this study are provided in Table 1. BAT-26 singleplex: SEQ IDs. 1-4; ACVR2A singleplex: SEQ IDs. 5-8; DEFB105A/B singleplex: SEQ IDs. 9-12; BRAF V600E singleplex: SEQ ID. 13-16; BAT-26-ACVR2A-DEFB105A/B triplex: SEQ IDs. 1-5, 7, 9, 11, 17-20. Desalted primers and HPLC-purified probes were manufactured by Invitrogen and Applied Biosystems UK.

ddPCR Conditions

Droplet digital PCR (ddPCR) was performed using the Bio-Rad QX100 system as instructed by the manufacturer. PCR reactions were prepared in a 20 μL volume containing 10 μL of 2× Supermix for Probes without dUTP (Bio-Rad ref. 1863024), 900 nM of each primer, 250 nM of each TaqMan® probe and up to 16.5 ng of DNA template, which is equivalent to 5,000 copies. The PCR reaction was then transferred to a disposable droplet generator cassette (Bio-Rad ref. 864008). 70 μL of droplet generation oil (Bio-Rad ref. 1863005) was added and the cassette loaded into the droplet generator. Generated droplets (40 μL) were transferred to a 96-well PCR plate (Eppendorf ref. 0030 128.575). Emulsified PCR reactions were then run on a C1000 thermal cycler (Bio-Rad) under the following cycling conditions: denaturation at 95° C. for 10 min followed by 40 amplification cycles of 94° C. for 30 sec, 61° C. for 3 min (BAT-26) or 59° C. for 3 min (DEFB105A/B) or 55° C. for 3 min (ACVR2A) or 60° C. for 1 min (BRAFV600E); final hold at 98° C. for 10 min. Ramp rate was set to 2.5° C./sec. At each run, controls with no DNA and controls containing 100% WT or 100% mutant DNA were included. Cluster thresholding and quantification was performed with the QuantaSoft v1.7.4 software (Bio-RAD). For the ddPCR MSI assays, droplets were manually assigned as WT or MSI positive based on their fluorescence amplitude: WT, VIC$^+$/FAM$^+$; MSI positive (mutant), VIC$^+$/FAM$^{-/low}$. Droplets with no template were assigned VIC$^-$/FAM$^-$. Assay optimization was performed with genomic DNA (gDNA) of HCT-116 cell line (a MSI positive colon cancer cell line) diluted or not in WT DNA obtained from peripheral blood mononuclear cells (PBMC). From droplets counts through manual assignment, mutant allele frequencies (MAF) were determined.

LOB and LOD Calculations

The background signal or false-positive rate of each assay was estimated using at least 53 replicates of WT DNA. The limit of blank (LOB) was defined as the upper 95% confidence limit of the mean false-positive measurements. The analytical sensitivity was estimated using serial dilutions of HCT-116 cell line in WT DNA, in mutant allele frequencies (MAF) ranging from 10% to 0.01% (1:2 serial dilutions). The total number of replicates per dilution point ranged from 3 to 8 (10% and 5%, 3×; 2.5% and 1.25%, 4×; 0.63% to 0.16%, 6×; 0.08% to 0.01%, 8×) in order to maximize the detection of rare events. The limit of detection (LOD) was estimated as the lowest mutant concentration likely to be reliably distinguished from the LOB.

Validation of the ddPCR MSI Assays in Patient Samples

Formalin-fixed paraffin-embedded (FFPE) tumor tissue, plasma or serum samples of patients with predominantly colorectal cancer (CRC) or endometrial carcinomas (EC) were used to validate the ddPCR MSI assays. All samples were obtained from patients treated and enrolled in clinical studies at the Institut Curie (Paris, France), with approval from the Institution's Clinical Research Ethical Board. Samples were selected from a pool of microsatellite stable (MSS) or microsatellite instable (MSI-H) tumors, identified by the pentaplex PCR method (Bacher et al 2004) in association or not with immunohistochemistry staining (IHC) of mismatch repair (MMR) proteins (MLH1, MSH2, MHS6 and PMS2). gDNA from tumor tissues was extracted using the Qiagen DNA FFPE Tissue Kit (Qiagen ref. 56404) according to the manufacturer's instructions and stored at −20° C. cfDNA was extracted from 0.5 to 1.8 mL of plasma or serum using the QIAamp® Circulating Nucleic Acid Kit (Qiagen ref. 55114), following the manufacturer's recommendations and stored at −20° C. DNA was quantified using Qubit dsDNA HS assay and LINE-1 amplification (Rago et al 2007). ddPCR reactions were performed as described above. Total DNA amount per reaction varied from 2.5 ng to 10 ng for FFPE samples and from 1 ng to 10 ng for plasma or serum samples.

Results

BAT-26, ACVR2A and DEFB105A/B MSI ddPCR Assays Reliably Detect Allele Size Variations in the Microsatellites Located Inside MSH2, ACVR2A and DEFB105A and B Genes, Respectively We developed ddPCR assays capable of detecting allele size variations for 3 mononucleotide poly(A) microsatellite (MS) markers: BAT-26, a quasi-monomorphic long $A_{27}$ repeat located at the fifth intron of MSH2 gene, and two shorter $A_8$ and $A_9$ repeats located in the tenth exon of ACVR2A and second intron of DEFB105A/B paralogous genes, respectively (Table 1). BAT-26 is one of the five microsatellite markers widely used to determine the MSI status of colorectal and endometrial tumors in clinical practice (Suraweera et al 2002). The microsatellites located within ACVR2A and DEFB105A/B genes are novel discriminatory markers recently identified from the analysis of TCGA exome sequencing data as recurrently unstable in MSI-H tumors, as compared to MSS tumors (Hause et al 2016; Maruvka et al 2017). The three assays are based on the drop-off ddPCR strategy, which identifies mutated alleles based on the absence of a WT signal (Decraene et al 2018). For each microsatellite marker two Taqman hydrolysis probes were designed within the same amplicon. A VIC labelled reference probe (REF), which hybridizes to a non-variable sequence upstream or downstream of the microsatellite region and a FAM labelled drop-off probe (MS), which covers the entire poly-A homopolymer plus 2 to 4 bases on either side to confer its ability to bind properly and the resulting destabilization in case of mutated alleles associated with microsatellite instability. While the REF probe quantifies the total number of copies of the amplicon (i.e. BAT-26, ACVR2A or DEFB105A/B DNA fragments), the MS probe discriminates WT and MSI alleles due to inefficient hybridization to mutant sequences. Therefore, with this type of assay 2-D scatter plots of VIC and FAM fluorescence amplitude may show three possible clusters of droplets: droplets with no template (VIC$^-$/FAM$^-$), droplets containing WT alleles (VIC$^+$/FAM$^+$) and droplets containing MSI positive alleles (VIC$^+$/FAM$^{-/low}$) (FIGS. 1A to 1I).

Given the low complexity of the MS probe, adjustments to standard ddPCR conditions (BioRAD guidelines) had to be made in order to achieve specific hybridization to WT alleles. We observed that a thermal cycling protocol with increased annealing temperature and annealing/extension time improved significantly the specificity of the MS probe to WT alleles and, accordingly, improved the separation of the WT and MSI-positive clouds. Optimized assays were able to specifically detect MSI alleles in DNA extracted from HCT-116 MSI-H cell line while no instability could be observed in WT DNA derived from peripheral blood mononuclear cells (PBMC) (FIGS. 1A and 1B for BAT-26; 1D and 1E for DEFB105A/B; 1G and 1H for ACVR2A). Moreover, the three assays were able to accurately quantify MSI alleles in 1/10 dilutions of HCT-116 cell line in a WT background (FIGS. 1C, 1F, 1I).

BAT-26, ACVR2A and DEFB105A/B ddPCR Assays are Highly Specific and Reach a Limit of Detection Below 0.1%

Analytical specificity of BAT-26, ACVR2A and DEFB105A/B ddPCR MSI assays was evaluated by measuring false-positive MSI calls in at least 53 individual ddPCR reactions of WT DNA derived from PBMCs (average number of copies per reaction: 4520 for BAT-26; 3380 for ACVR2A and 3740 for DEFB105A/B). Mean false positive rates were: 0.006908±0.01366% for BAT-26 (MSI calls in 11/53 reactions), 0.006136±0.01623% for ACVR2A (MSI calls in 7/55 reactions) and 0.005604±0.01911% for DEFB105A/B (MSI calls in 5/55 reactions). The limit of blank (LOB) of each assay was estimated at 0.01067% for BAT-26 (FIG. 2A), 0.01077% for DEFB105A/B (FIG. 2B) and 0.01052% for ACVR2A (FIG. 2C). The analytical sensitivity was estimated using serial dilutions of HCT-116 cell line in WT PBMC DNA, in mutant allele frequencies (MAF) ranging from 10% to 0.01% (1:2 serial dilutions). The total number of replicates per dilution point ranged from 3 to 8 (10% and 5%, 3×; 2.5% and 1.25%, 4×; 0.63% to 0.16%, 6×; 0.08% to 0.01%, 8×) in order to maximize the detection of rare events. For the three assays, excellent linear correlations were observed between the expected and observed MAF, indicating that the three assays can accurately quantify MSI in a wide range of frequencies, $R^2=0.9984$ $p<0.0001$ for BAT-26 (FIG. 2A), $R^2=0.9964$ $p<0.0001$ for DEFB105A/B (FIG. 2B) and $R^2=0.9955$ $p<0.0001$ for ACVR2A (FIG. 2C). The limit of detection (LOD), estimated as the lowest mutant concentration likely to be accurately distinguished from the LOB was estimated at 0.04% for BAT-26 (FIG. 2A) and 0.08% for both DEFB105A/B (FIG. 2B) and ACVR2A markers (FIG. 2C). We conclude that the three MSI ddPCR assays are both highly sensitive and specific, promising better diagnostic accuracy and the unprecedented use of a MSI biomarker in liquid biopsies for diagnosis and monitoring of disease treatment and progression.

ddPCR MSI Testing in Clinical Samples

We next evaluated the performance of the BAT-26, ACVR2A and DEFB105A/B ddPCR MSI assays in 177 FFPE tumor samples obtained predominantly from patients with colorectal or endometrial cancers (Table 2). These samples had been previously characterized as MSI positive (MSI-H, n=94) or MSI negative (MSS, n=83) using the standard multiplex-PCR capillary electrophoresis method which evaluates microsatellite instability in 5 microsatellite markers: BAT-26, NR-21, BAT-25, MONO-27 and NR-24. Samples showing instability for at least 2 of the 5 markers were considered MSI positive (MSI-H), while samples showing no instability were classified as MSI negative (MSS). Importantly, ddPCR and following analyses were performed blindly, without knowledge of the MSI status of samples. As shown in Table 2, MSI ddPCR identified unstable alleles for BAT-26, ACVR2A and DEFB105A/B markers in 92, 87 and 81 samples, respectively. Noteworthy for BAT-26 concordant results between capillary electrophoresis and ddPCR were obtained for 172 out of the 177 samples tested. For 3 of the 5 discordant samples, BAT-26 status could not be determined by capillary electrophoresis, but was defined as unstable by ddPCR. For the other 2 discordant samples, BAT-26 was classified as unstable by capillary electrophoresis but was reported as stable and undetermined by ddPCR. Considering a sample as MSI-H if instability was found for at least 2 out of the 3 ddPCR markers analyzed, MSI ddPCR could correctly classify 100% (83/83) of the MSS samples as MSS and 94% (88/94) of the MSI-H samples as MSI-H. Of note, most of the discordant cases corresponded to endometrial tumor samples (4/6) which are more difficult to classify than colorectal cancers and more prone for false-negative results (Suraweera et al 2002; Wang et al 2017).

Given the high sensitivity and specificity of the MSI ddPCR assays, we next evaluated their performance on 22 plasma or serum samples collected from 12 patients with stage IV MSI-H colorectal or endometrial tumors. Notable MSI ddPCR assays were able to detect microsatellite instability in all the samples tested, including samples with low mutant allele frequencies, close to 0.2% (Table 3). Moreover, five of these 12 patients had BRAF mutated tumors (BRAF V600E). Therefore, mutant allele frequencies reported by the MSI ddPCR assays could be directly compared with the ones obtained with a ddPCR assay that targets specifically BRAF V600E mutation. Excellent correlations were obtained ($R^2=0.9852$ $p<0.0001$ for BAT-26, $R^2=0.9603$ $p<0.0001$ for ACVR2A and $R^2=0.9275$ $p<0.0001$ for DEFB105A/B), which further supports the reliability of the ddPCR MSI assays for detection and quantification of circulating tumor DNA (FIGS. 3A to 3C).

Taken together, these results demonstrate that the MSI ddPCR assays can accurately detect MSI in patient samples and therefore, can be used as an alternative method for MSI testing in tumor tissue and liquid biopsies in clinical practice.

Development of a Multiplex Assay

We next aimed at developing a multiplex MSI ddPCR assay that can simultaneously detect MSI status for BAT-26, ACVR2A and DEFB105A/B markers in a single reaction. The multiplex strategy consisted in varying the concentrations of primers and probes in order to change end-point fluorescence so that WT and MSI-positive clusters of droplets for the 3 markers could be distinguished from each other (see Bio-Rad droplet digital PCR multiplexing guideline). Different primers and probes as well as diverse combinations of primer and probe concentration, annealing temperature and extension time were tested, some of which generated satisfactory results. One example, obtained with annealing/extension temperature/time at 63° C. for 3 min and the following primer/probe combinations: BAT-26, SEQ IDs. 1-4, 0.2×; ACVR2A, SEQ IDs. 5, 7, 17 and 18, 0.6× and DEFB105A/B, SEQ IDs. 9, 11, 19 and 20, 1× is presented in FIG. 4. These results, although preliminary, demonstrate the feasibility of multiplexing ddPCR assays targeting diverse microsatellite sequences in a single reaction.

TABLE 1

List of primers and probes

| | | |
|---|---|---|
| BAT-26 Primer Fw | SEQ ID NO. 1 | GACTTCAGCCAGTATATGAAATTGGATATTG |
| BAT-26 Primer Rev | SEQ ID NO. 2 | GTATATGTCAATGAAAACATTTTTTAACCATTCAAC |
| BAT-26 Probe REF | SEQ ID NO. 3 | VIC-AGCAGTCAGAGCCCTTAACCTTT-MGB-NFQ |
| BAT-26 Probe MS | SEQ ID NO. 4 | FAM-AGGTAAAAAAAAAAAAAAAAAAAAAAAAAAGG-MGB-NFQ |
| ACVR2A Primer Fw | SEQ ID NO. 5 | GAGGAGGAAATTGGCCAGCATC |
| ACVR2A Primer Rv | SEQ ID NO. 6 | AGCTAACTGGATAACTTACAGCATG |

TABLE 1-continued

List of primers and probes

| | | |
|---|---|---|
| ACVR2A Probe REF | SEQ ID NO. 7 | VIC-ACTTCCTGCATGTCTTCAAGAG-MGB-NFQ |
| ACVR2A Probe MS | SEQ ID NO. 8 | FAM-CCTCTTTTTTTTATGC-MGB-NFQ |
| DEFB105A/B Primer Fw | SEQ ID NO. 9 | TTGAAAAATCTGGGCTGATTCTTGA |
| DEFB105A/B Primer Rev | SEQ ID NO. 10 | TGAGGGAGCTTTCCAGGAAATG |
| DEFB105A/B Probe REF | SEQ ID NO. 11 | VIC-CTTTGACATGTTCCCCATTTCTAG-MGB-NFQ |
| DEFB105A/B Probe MS | SEQ ID NO. 12 | FAM-TCCCTTTTTTTTTGGT-MGB-NFQ |
| BRAF Primer Fw | SEQ ID NO. 13 | TGAAGACCTCACAGTAAAAATAGGTGA |
| BRAF Primer Fw | SEQ ID NO. 14 | ACTGATGGGACCCACTCCATC |
| BRAF Probe WT | SEQ ID NO. 15 | VIC-TAGCTACAGTGAAAT-MGB-NFQ |
| BRAF Probe V600E | SEQ ID NO. 16 | FAM-CTAGCTACAGAGAAAT-MGB-NFQ |
| ACVR2A Primer Rv-1 | SEQ ID NO. 17 | CAGCATGTTTCTGCCAATAATCTC |
| ACVR2A Probe MS-1 | SEQ ID NO. 18 | FAM-AGGCCTCTTTTTTTATG-MGB-NFQ |
| DEFB105A/B Primer Rev-1 | SEQ ID NO. 19 | GCCAAGAAAGAGCTGCTGAG |
| DEFB105A/B Probe MS-1 | SEQ ID NO. 20 | FAM-AACTGTCCCTTTTTTTTGGT-MGB-NFQ |

TABLE 2

Instability patterns obtained by pentaplex-PCR (*BAT-26, NR-21, BAT-25, Mono-27 and NR-24) and ddPCR MSI assays in FFPE tumor samples.

| | Pentaplex | | ddPCR | | | |
|---|---|---|---|---|---|---|
| Tumor | Profile* | Classification | BAT-26 | ACVR2A | DEFB105 | Classification |
| colon | ND++++ | MSI-H | + | + | + | MSI-H |
| colon | +++++ | MSI-H | + | + | + | MSI-H |
| colon | +++++ | MSI-H | + | + | − | MSI-H |
| colon | +++++ | MSI-H | + | − | + | MSI-H |
| colon | +++++ | MSI-H | + | − | + | MSI-H |
| colon | +++++ | MSI-H | + | + | + | MSI-H |
| colon | +++++ | MSI-H | + | − | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | ND++++ | MSI-H | + | + | + | MSI-H |
| colon | +++++ | MSI-H | + | + | + | MSI-H |
| colon | ++-++ | MSI-H | + | + | + | MSI-H |
| colon | +++++ | MSI-H | + | + | + | MSI-H |
| colon | +++-- | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | ++++- | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | ++++- | MSI-H | + | + | + | MSI-H |
| colon | +++++ | MSI-H | + | + | + | MSI-H |

TABLE 2-continued

Instability patterns obtained by pentaplex-PCR (*BAT-26, NR-21, BAT-25, Mono-27 and NR-24) and ddPCR MSI assays in FFPE tumor samples.

| Tumor | Pentaplex | | ddPCR | | | |
| --- | --- | --- | --- | --- | --- | --- |
| | Profile* | Classification | BAT-26 | ACVR2A | DEFB105 | Classification |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +−+++ | MSI-H | + | + | + | MSI-H |
| colon | +++ ++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| colon | +++++ | MSI-H | + | + | + | MSI-H |
| endometrial | +−−+− | MSI-H | + | + | − | MSI-H |
| endometrial | +++++ | MSI-H | + | + | + | MSI-H |
| endometrial | ND++++ | MSI-H | ND | + | + | MSI-H |
| endometrial | +++++ | MSI-H | + | + | + | MSI-H |
| endometrial | +−−++ | MSI-H | + | + | − | MSI-H |
| endometrial | ND++++ | MSI-H | + | + | − | MSI-H |
| endometrial | +++++ | MSI-H | + | − | + | MSI-H |
| endometrial | +−+−+ | MSI-H | + | + | − | MSI-H |
| endometrial | +++++ | MSI-H | + | + | − | MSI-H |
| endometrial | +++++ | MSI-H | + | + | − | MSI-H |
| endometrial | +−+−+ | MSI-H | + | + | + | MSI-H |
| endometrial | +++++ | MSI-H | + | + | + | MSI-H |
| endometrial | +++++ | MSI-H | + | + | + | MSI-H |
| endometrial | +++++ | MSI-H | + | + | + | MSI-H |
| endometrial | +++++ | MSI-H | + | + | + | MSI-H |
| endometrial | +++++ | MSI-H | + | + | + | MSI-H |
| cholangiocarcinoma | +++++ | MSI-H | + | + | + | MSI-H |
| intestine | +++++ | MSI-H | + | + | + | MSI-H |
| rectum | +++++ | MSI-H | + | + | + | MSI-H |
| rectum | +++++ | MSI-H | + | + | + | MSI-H |
| sebaceome | +−++− | MSI-H | + | + | + | MSI-H |
| stomach | +++++ | MSI-H | + | + | + | MSI-H |
| colon | ND+ND+− | MSI-H | ND | − | − | MSS |
| ovary | ND−+++ | MSI-H | ND | + | − | MSS |
| endometrial | +++++ | MSI-H | ND | + | − | MSS |
| endometrial | +++++ | MSI-H | + | − | − | MSS |
| endometrial | +−+−− | MSI-H | − | − | − | MSS |
| endometrial | ++ + + + | MSI-H | + | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |
| colon | −−−−− | MSS | − | − | − | MSS |

TABLE 2-continued

Instability patterns obtained by pentaplex-PCR (*BAT-26, NR-21, BAT-25, Mono-27 and NR-24) and ddPCR MSI assays in FFPE tumor samples.

| Tumor | Pentaplex Profile* | Classification | ddPCR BAT-26 | ACVR2A | DEFB105 | Classification |
|---|---|---|---|---|---|---|
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | ----- | MSS | − | − | − | MSS |
| colon | +---- | MSS | + | − | − | MSS |
| colon | +---- | MSS | + | − | − | MSS |
| colon | +---- | MSS | + | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | − | − | MSS |
| endometrial | ----- | MSS | − | + | − | MSS |
| ovary | ----- | MSS | − | − | − | MSS |
| ovary | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| rectum | ----- | MSS | − | − | − | MSS |
| pancreas | ----- | MSS | − | − | − | MSS |
| pancreas | ----- | MSS | − | − | − | MSS |
| rectum | ----- | MSS | − | − | − | MSS |

ND: non determined

TABLE 3

Mutant allele frequencies obtained by ddPCR MSI assays in body fluid samples collected from patients with stage IV MSI-H colorectal or endometrial tumors. Patients with BRAF$^{V600E}$ mutated tumors are marked by an asterisk

| Patient | Primary tumor | Sampling | Sample | MSI-ddPCR MAF (%) | | |
|---|---|---|---|---|---|---|
| | | | | BAT-26 | DEFB106 | ACVR2A |
| P-01* | colon | before treatment | plasma | 25.74 | 19.80 | 22.30 |
| | | progression | plasma | 0.35 | 0.32 | 0.43 |
| P-02 | colon | pre-surgery | serum | 0.52 | 0.62 | 0.66 |
| | | pre-surgery | serum | 0.23 | — | — |
| P-03 | colon | 1$^{st}$ progression | serum | 4.20 | 2.88 | — |
| | | 2$^{nd}$ progression | serum | — | 0.21 | — |
| | | before treatment | plasma | 62.00 | 50.88 | 53.10 |
| P-04* | colon | treatment | plasma | 0.45 | 0.39 | 0.28 |
| | | treatment | plasma | 2.80 | 2.10 | 2.60 |
| | | progression | plasma | 1.70 | — | 2.90 |
| | | treatment | plasma | 2.09 | 1.40 | 1.90 |
| P-05* | colon | treatment | plasma | 6.80 | 4.07 | 5.30 |
| | | treatment | plasma | 0.26 | — | 0.23 |
| P-06* | colon | treatment | plasma | 11.40 | — | 6.60 |
| | | treatment | plasma | 13.10 | — | 5.50 |
| P-07 | colon | before treatment | plasma | 45.27 | 13.52 | 37.90 |
| P-08* | endometrium | treatment | plasma | 1.82 | 0.24 | 1.47 |
| P-09 | endometrium | pre-surgery | serum | 5.70 | 1.05 | 1.60 |
| P-10 | endometrium | pre-surgery | plasma | 0.65 | — | |
| P-11 | endometrium | pre-surgery | serum | 0.25 | — | |
| P-12 | endometrium | pre-surgery | serum | 1.32 | — | |
| | | pre-surgery | serum | — | 0.31 | — |

REFERENCES

Hause R J, Pritchard C C, Shendure J, Salipante S J (2016) Classification and characterization of microsatellite instability across 18 cancer types. Nature Medicine 22(1): 1342-1350

Rago C, Huso D L, Diehl F, Karim B, Liu G, Papadopoulos N, Samuels Y, Velculescu V E, Vogelstein B, Kinzler K W, Diaz L A Jr (2007) Serial assessment of human tumor burdens in mice by the analysis of circulating DNA. Cancer Research 67(19:9364-9370

Suraweera N, Duval A, Reperant M, Vaurt C, Furlan D, Leroy K, Seruca R, Lacopetta B, Hamelin R (2002) Evaluation of tumor microsatellite instability using five quasimonomorphic mononucleotide repeats and pentaplex PCR. Gastroenterology 123:1804-1811

Maruvka Y, Mouw K W, Karlic R, Parasuraman P, Kamburov A, Polak P, Haradhvala N J, Hess J M, Rheinbay E, Brody Y, Koren A, Braunstein L Z, D'Andrea A, Lawrence M S, Bass A, Bernards A, Michor F, Getz G (2017) Analysis of somatic microsatellite indels identifies driver events in human tumors. Nature Biotechnology 35:951-959

Decraene C, Silveira A B, Bidard F C, Vallée A, Michel M, Melaabi S, Vincent-Salomon A, Saliou A, Houy A, Milder M, Lantz O, Ychou M, Denis M G, Pierga J Y, Stern M H, Proudhon C (2018) Multiple hotspot mutations scanning by single droplet digital PCR. Clinical Chemistry 64:317-328

Wang Y, Shi C, Eisenberg R, Vnencak-Jones C L (2017) Differences in microsatellite instability profiles between endometrioid and colorectal cancers. The Journal of Molecular Diagnostics 19:57-64

The invention claimed is:

1. A method for detecting a mutation in a microsatellite sequence locus of a target fragment from a DNA sample, comprising a step of subjecting said DNA sample to a digital polymerase chain reaction (dPCR) in the presence of a PCR solution comprising:
- a pair of primers suitable for amplifying said target fragment of the DNA sample including said microsatellite sequence;
- a first MS oligonucleotide (MS) hydrolysis probe, labeled with a first fluorophore, wherein said first MS hydrolysis probe is complementary to a wild-type sequence including the microsatellite sequence, wherein said MS hydrolysis probe is designed to confer its ability to bind properly to the wild-type microsatellite sequence while preventing hybridization in the presence of a mutation in the microsatellite sequence;
- and wherein the MS hydrolysis probe covers the full wild-type microsatellite sequence and extends further between 1 to 10 nucleotides on each extremity; and
- a second reference oligonucleotide hydrolysis probe, labeled with a second fluorophore, wherein said second reference oligonucleotide hydrolysis probe is complementary to a wild-type sequence of said target DNA fragment located outside of said microsatellite sequence and wherein said hydrolysis probes have a fluorophore covalently attached to their 5'-end of the oligonucleotide probe and a quencher, and said method further comprises a step of measuring the fluorescence signals associated with the reference oligonucleotide hydrolysis and MS probes, wherein the maximal fluorescence intensity signal associated with both the reference oligonucleotide hydrolysis and MS probes indicates the presence of a wild-type microsatellite sequence in the target DNA fragment, while a shift in the fluorescence intensity signal associated with the MS probe indicates the presence of a mutation in the microsatellite sequence of the target DNA fragment.

2. The method according to claim 1, wherein the target fragment of the DNA sample is constitutional genomic DNA.

3. The method according to claim 1, wherein the target fragment of the DNA sample is genomic tumor DNA.

4. The method according to claim 1, wherein the microsatellite sequence locus is selected from the group consisting of: BAT-25, BAT-26, BAT-34c4, BAT-40, NR21, NR24, MONO-27, D2S123, D5S346, D17S250, ACVR2A, DEFB105A, DEFB105B, RNF43, DOCK3, GTF2IP1, LOC100093631, PIP5K1A, MSH3, TRIM43B, PPFIA1 and TDRD1.

5. The method according to claim 1, wherein the DNA sample is selected from the group consisting of tumor tissue, disseminated cells, feces, blood cells, blood plasma, serum, lymph nodes, urine, saliva, semen, stool, sputum, cerebrospinal fluid, tears, mucus, pancreatic juice, gastric juice, amniotic fluid, cerebrospinal fluid, and serous fluids.

6. The method according to claim 1, wherein the target fragment is originating from a tumor in a patient with cancer, a disease associated with mismatch repair (MMR) genes or familial tumor predisposition.

7. A method for prognosis of cancers comprising the detection of a mutation in a microsatellite sequence locus of a target fragment from a DNA sample according to claim 1, wherein the target fragment is originating from a tumor.

8. A method for predicting the efficacy of a treatment in a subject suffering from a cancer, comprising the detection of a mutation in a microsatellite sequence locus of a target fragment from a DNA sample according to claim 1, wherein the target fragment is originating from a tumor and wherein the treatment is optionally immune therapy optionally immune checkpoint therapy.

9. The method according to claim 1, wherein the target fragment of the DNA sample originates from a tumor in a patient diagnosed with a tumor associated with impaired DNA mismatch repair.

* * * * *